(12) United States Patent
Sato et al.

(10) Patent No.: US 7,471,502 B2
(45) Date of Patent: Dec. 30, 2008

(54) IONIC LIQUIDS, ELECTROLYTE SALTS FOR ELECTRICAL STORAGE DEVICES, LIQUID ELECTROLYTES FOR ELECTRICAL STORAGE DEVICES, ELECTRICAL DOUBLE-LAYER CAPACITORS, AND SECONDARY BATTERIES

(75) Inventors: Takaya Sato, Chiba (JP); Gen Masuda, Chiba (JP); Ryutaro Nozu, Chiba (JP); Tatsuya Maruo, Chiba (JP)

(73) Assignee: Nisshinbo Industries, Inc., Tokyo (JP)

( * ) Notice: Subject to any disclaimer, the term of this patent is extended or adjusted under 35 U.S.C. 154(b) by 285 days.

(21) Appl. No.: 11/537,269

(22) Filed: Sep. 29, 2006

(65) Prior Publication Data

US 2007/0031729 A1 Feb. 8, 2007

Related U.S. Application Data

(62) Division of application No. 10/472,823, filed as application No. PCT/JP02/02845 on Mar. 25, 2002, now Pat. No. 7,297,289.

(30) Foreign Application Priority Data

Mar. 26, 2001 (JP) ............................. 2001-087221
Sep. 10, 2001 (JP) ............................. 2001-272834

(51) Int. Cl.
H01G 9/00 (2006.01)

(52) U.S. Cl. ................... 361/502; 361/503; 361/504; 361/508; 361/512; 361/523; 429/314; 429/322; 429/324; 429/342; 252/62.2

(58) Field of Classification Search ................. 361/502, 361/503–504, 523–525, 528–534; 252/62.2; 429/314, 322, 324, 342
See application file for complete search history.

(56) References Cited

U.S. PATENT DOCUMENTS 2,941,966 A 6/1960 Campbell (Continued)

FOREIGN PATENT DOCUMENTS

EP 0 660 345 A1 6/1995

(Continued)

OTHER PUBLICATIONS

A.B. McEwen et al., Journal of the Electrochemical Society, vol. 146, No. 5, 1999, pp. 1687-1695.

(Continued)

*Primary Examiner*—Nguyen T Ha
(74) *Attorney, Agent, or Firm*—Birch, Stewart, Kolasch & Birch, LLP

(57) ABSTRACT

Electrical storage devices having excellent low-temperature properties can be obtained by using a quaternary salt (or ionic liquid) of general formula (1) below as an electrolyte salt for electrical storage devices or a liquid electrolyte for electrical storage devices.

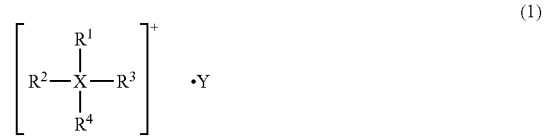

(1)

In formula (1), $R^1$ to $R^4$ are each independently an alkyl group of 1 to 5 carbons or an alkoxyalkyl group of the formula $R'—O—(CH_2)_n—$, with the proviso that at least one group from among $R^1$ to $R^4$ is the above alkoxyalkyl group. X is a nitrogen or phosphorus atom, and Y is a monovalent anion.

20 Claims, 12 Drawing Sheets

U.S. PATENT DOCUMENTS

| | | | |
|---|---|---|---|
| 4,482,713 | A | 11/1984 | Strickler |
| 4,725,926 | A | 2/1988 | Morimoto et al. |
| 6,015,638 | A * | 1/2000 | Ventura et al. .............. 429/307 |
| 6,574,092 | B2 * | 6/2003 | Sato et al. ................... 361/502 |
| 6,841,299 | B2 * | 1/2005 | Wariishi ..................... 429/188 |
| 6,949,317 | B2 * | 9/2005 | Yoshida et al. ............. 429/303 |
| 7,154,737 | B2 * | 12/2006 | Maruo et al. ................ 361/502 |

FOREIGN PATENT DOCUMENTS

| | | | |
|---|---|---|---|
| JP | 47-33279 | | 8/1972 |
| JP | 58-10542 | A | 1/1983 |
| JP | 61-32509 | A | 2/1986 |
| JP | 62-252927 | A | 11/1987 |
| JP | 63-173312 | A | 7/1988 |
| JP | 04-349365 | A | 12/1992 |
| JP | 07-161588 | A | 6/1995 |
| JP | 10-55717 | A | 2/1998 |
| JP | 11-224831 | A | 8/1999 |
| JP | 11-260400 | A | 9/1999 |
| JP | 11-297355 | A | 10/1999 |
| JP | 11-307121 | A | 11/1999 |

OTHER PUBLICATIONS

H. Matsumoto et al., "Yoyuen oyobi Koon Kagaku (Molten Salt and Pyrochemical)", vol. 44, No. 1, 2001, pp. 7-18, by Molten Salt Committee of the Electrochemical Society of Japan.

Z.B. Zhou et al., Chemistry Letters, vol. 33, No. 7, 2004, pp. 886-887.

Certificate of Experimental Results, Stella Chemifa Corporation, Dec. 22, 2004.

Cooper et al., Solid State Ionics, vol. 18, No. 19, pp. 570-576 (1986).

Campbell et al., J. Org. Chem., vol. 28, No. 20, pp. 2069-2075 (1963).

Matsumoto et al., "Improvement of ionic conductivity of room temperature molten salt based on quaternary ammonium cation and imide anion," Electrochemical Society Proceedings, vol. 99-41, pp. 186-192, 2000.

Rios et al., "Generation and study of the reactivity of α-ammonium distonic radical cations in solution," Journal of American Chemical Society, vol. 118, No. 45, pp. 11313-11314, 1996.

Stuff et al., "A new room-temperature molten salt electrolyte," Journal of the Electrochemical Society, vol. 137, No. 5, pp. 1492-1493, 1990.

Cooper et al., "Versatile organic iodide melts and glasses with high mole fractions of lithium iodide: glass transition temperatures and electrical conductivities," Solid State Ionics, vol. 9 and 10, pp. 617-622, 1983.

* cited by examiner

IONIC LIQUIDS, ELECTROLYTE SALTS FOR ELECTRICAL STORAGE DEVICES, LIQUID ELECTROLYTES FOR ELECTRICAL STORAGE DEVICES, ELECTRICAL DOUBLE-LAYER CAPACITORS, AND SECONDARY BATTERIES

This application is a Divisional of co-pending application Ser. No. 10/472,823 filed on Sep. 25, 2003 and for which priority is claimed under 35 U.S.C. § 120. Application Ser. No. 10/472,823 is the national phase of PCT International Application No. PCT/JP02/02845 filed on Mar. 25, 2002 under 35 U.S.C. § 371. The entire contents of each of the above-identified applications are hereby incorporated by reference.

TECHNICAL FIELD

The present invention relates to ionic liquids, electrolyte salts for electrical storage devices, liquid electrolytes for electrical storage devices, electrical double-layer capacitors, and secondary batteries.

BACKGROUND ART

An ionic compound generally forms crystals in which positively charged cations and negatively charged anions pull electrostatically against each other. When this ionic compound is dissolved in various other liquids, including water, it provides a liquid that carries electricity; that is, an electrolyte solution. Electrolyte solutions obtained by dissolving an ionic compound in an organic solvent are commonly used in, for example, nonaqueous electrolyte batteries and capacitors.

Some ionic compounds, when the temperature is raised, undergo activation of thermal motion to such an extent as to overcome the ionic interactions, causing the compound itself to become liquid and capable of carrying electricity. A salt in such a state is generally referred to as a "molten salt."

The chemical species present in the molten salt are all charged cations or anions; no neutral atoms or molecules are present. Therefore, elements which cannot be obtained from an aqueous electrolyte solution because they have too large a reducing or oxidizing power with respect to water, including metals such as alkali metals, aluminum and rare-earth elements, and non-metals such as fluorine, can be electrolyzed in a molten salt and obtained in elemental form. This has become a main industrial application of molten salts.

Some such molten salts maintain a liquid state at room temperature and do not solidify even at very low temperatures. Such molten salts which maintain a liquid state at room temperature or lower are referred to in particular as "room-temperature molten salts" or "ionic liquids." To minimize electrostatic interactions between the cations and anions which make up the ionic liquid, either or both are molecular ions of a substantial size, and are moreover monovalent to minimize the charge and electrostatic interactions.

Research is actively being pursued on applications for such ionic liquids in electrolytic deposition and in electrolytes for batteries and other purposes. However, because ionic liquids generally have a high moisture absorption and are difficult to handle in air, such applications has yet to be fully realized.

In light of the above, the 1-ethyl-3-methylimidazolium tetrafluoroborate reported by Wilkes et al. in 1992 is a remarkable ionic liquid that can be handled even in air. This new ionic liquid led to the synthesis of many ionic liquids which are combinations of numerous alkylimidazolium cations having different side chains with various anions. Although the properties and applications for these ionic liquids are being actively investigated, there exists a desire for the development of various ionic liquids that can be more conveniently produced and are easy to handle.

Nonaqueous liquid electrolyte-type electrical double-layer capacitors can be charged and discharged at a high current, and thus hold considerable promise as energy storage devices for such applications as electrical cars and auxiliary power supplies.

Prior-art nonaqueous liquid electrolyte-type electrical double-layer capacitors are constructed of positive and negative polarizable electrodes made primarily of a carbonaceous material such as activated carbon and a nonaqueous electrolyte solution. The composition of the nonaqueous electrolyte solution is known to have a large influence on the withstand voltage and electrostatic capacitance of the capacitor.

The nonaqueous electrolyte solution is composed of an electrolyte salt and a nonaqueous organic solvent. Studies have been conducted on various combinations of such electrolyte salts and nonaqueous organic solvents.

For example, quaternary ammonium salts (e.g., JP-A 61-32509, JP-A 63-173312, JP-A 10-55717) and quaternary phosphonium salts (e.g., JP-A 62-252927) are commonly used as the electrolyte salt because of their solubility and degree of dissociation in organic solvents, as well as their broad electrochemical stability range. Organic solvents that are commonly used on account of their high dielectric constant, broad electrochemical stability range and high boiling point include ethylene carbonate, diethyl carbonate, propylene carbonate, butylene carbonate, γ-butyrolactone, acetonitrile and sulfolane.

However, in nonaqueous electrolyte-type electrical double-layer capacitors currently in use, the inadequate solubility of electrolyte salts (e.g., quaternary ammonium salts, quaternary phosphonium salts) in organic solvents commonly used for this purpose limits the amount of salt that can be added, resulting in nonaqueous electrolyte solutions of lower ionic conductivity and electrical double-layer capacitors of lower electrostatic capacitance.

Moreover, because the electrolyte salts have a low solubility, they tend to crystallize at low temperatures, compromising the low-temperature characteristics of the electrical double-layer capacitor.

In light of these circumstances, the objects of the invention are to provide ionic liquids which can be easily and efficiently produced, electrolyte salts for electrical storage devices which have excellent solubility in organic solvents for nonaqueous electrolyte solutions and have a low melting point, liquid electrolytes for electrical storage devices which include these electrolyte salts, and also electrical double-layer capacitors and secondary batteries of excellent low-temperature properties which are constructed using such liquid electrolytes.

We have conducted extensive investigations aimed at achieving the above objects, as a result of which we have discovered that some quaternary ammonium salts and quaternary phosphonium salts bearing at least one alkoxyalkyl substituent have low melting points and excellent characteristics as ionic liquids.

Moreover, we have found that, because quaternary ammonium salts and quaternary phosphonium salts bearing at least one alkoxyalkyl substituent have excellent solubility in nonaqueous organic solvents used in electrical storage devices and also have a low melting point, liquid electrolytes prepared using such quaternary salts can be obtained to a higher concentration than previously possible and are less likely to result in deposition of the electrolyte salt at low temperatures. We have also found that electrical double-layer capacitors manufactured using such liquid electrolytes have a high electrostatic capacitance and excellent low-temperature characteristics.

Accordingly, the present invention provides the following.

(1) An ionic liquid characterized by having general formula (1) below and a melting point of up to 50° C.

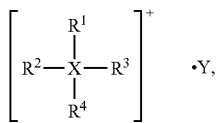

wherein $R^1$ to $R^4$ are each independently an alkyl of 1 to 5 carbons or an alkoxyalkyl of the formula $R'—O—(CH_2)_n—$, $R'$ being methyl or ethyl and the letter n being an integer from 1 to 4, and any two from among $R^1$, $R^2$, $R^3$ and $R^4$ may together form a ring, with the proviso that at least one of groups $R^1$ to $R^4$ is an alkoxyalkyl of the above formula; X is a nitrogen or phosphorus atom; and Y is a monovalent anion.

(2) The ionic liquid of (1) above which is characterized by having a melting point of up to 25° C.

(3) The ionic liquid of (1) or (2) above which is characterized in that X is a nitrogen atom.

(4) The ionic liquid of (3) above which is characterized in that X is a nitrogen atom, $R'$ is methyl, and the letter n is 2.

(5) The ionic liquid of (1) or (2) above which is characterized by having general formula (2) below

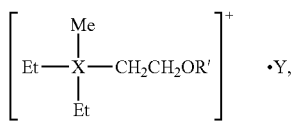

wherein $R'$ is methyl or ethyl, X is a nitrogen or phosphorus atom, Y is a monovalent anion, Me signifies methyl and Et signifies ethyl.

(6) The ionic liquid of any one of (1) to (5) above which is characterized in that Y is $BF_4^-$, $PF_6^-$, $(CF_3SO_2)_2N^-$, $CF_3SO_3^-$ or $CF_3CO_2^-$.

(7) The ionic liquid of (5) above which is characterized by Having general formula (3) below

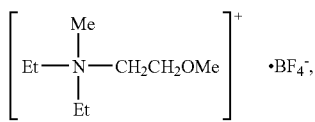

wherein Me signifies methyl and Et signifies ethyl.

(8) An electrolyte salt for electrical storage devices, which salt is characterized by being a quaternary salt of general formula (1) below

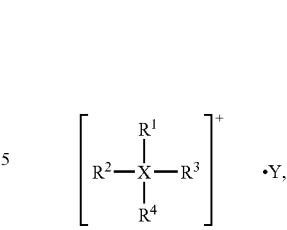

wherein $R^1$ to $R^4$ are each independently an alkyl of 1 to 5 carbons or an alkoxyalkyl of the formula $R'—O—(CH_2)_n—$, $R'$ being methyl or ethyl and the letter n being an integer from 1 to 4, and any two from among $R^1$, $R^2$, $R^3$ and $R^4$ may together form a ring, with the proviso that at least one of groups $R^1$ to $R^4$ is an alkoxyalkyl of the above formula; X is a nitrogen or phosphorus atom; and Y is a monovalent anion.

(9) The electrolyte salt for electrical storage devices of (8) above which is characterized by being a quaternary salt in which X is a nitrogen atom.

(10) The electrolyte salt for electrical storage devices of (9) above which is characterized by being a quaternary salt in which X is a nitrogen atom, $R'$ is methyl and the letter n is 2.

(11) The electrolyte salt for electrical storage devices of (8) above which is characterized by being a quaternary salt having general formula (2) below

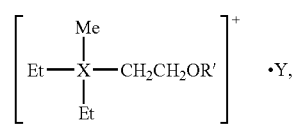

wherein $R'$ is methyl or ethyl, X is a nitrogen or phosphorus atom, Y is a monovalent anion, Me signifies methyl and Et signifies ethyl.

(12) The electrolyte salt for electrical storage devices of any one of (8) to (11) above which is characterized in that Y is $BF_4^-$, $PF_6^-$, $(CF_3SO_2)_2N^-$, $CF_3SO_3^-$ or $CF_3CO_2^-$.

(13) The electrolyte salt for electrical storage devices of (11) above which is characterized by having general formula (3) below

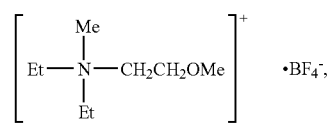

wherein Me signifies methyl and Et signifies ethyl.

(14) The electrolyte salt for electrical storage devices of any one of (8) to (13) above which is characterized by having a melting point of up to 25° C.

(15) A liquid electrolyte for electrical storage devices which is characterized by being composed solely of the ionic liquid of any one of (1) to (7) above.

(16) A liquid electrolyte for electrical storage devices which is characterized by being composed solely of the electrolyte salt for electrical storage devices of (14) above.

(17) A liquid electrolyte for electrical storage devices which is characterized by including at least one ionic liquid of any one of (1) to (7) above and a nonaqueous organic solvent.

(18) A liquid electrolyte for electrical storage devices which is characterized by including at least one electrolyte salt for electrical storage devices according to any one of (8) to (13) above and a nonaqueous organic solvent.

(19) The liquid electrolyte for electrical storage devices of (17) or (18) above which is characterized in that the nonaqueous organic solvent is a mixed solvent which includes as a main component ethylene carbonate or propylene carbonate.

(20) The liquid electrolyte for electrical storage devices of (17) or (18) above which is characterized in that the nonaqueous organic solvent is one selected from among ethylene carbonate, propylene carbonate, vinylene carbonate, dimethyl carbonate, ethyl methyl carbonate and diethyl carbonate, or a mixed solvent of two or more thereof.

(21) An electrical double-layer capacitor having a pair of polarizable electrodes, a separator between the polarizable electrodes and a liquid electrolyte, which electrical double-layer capacitor is characterized in that the liquid electrolyte is a liquid electrolyte for electrical storage devices according to any one of (15) to (20) above.

(22) The electrical double-layer capacitor of (21) above which is characterized in that the polarizable electrodes include as a main component a carbonaceous material prepared from a resin.

(23) The electrical double-layer capacitor of (22) above which is characterized in that the resin is a phenolic resin or a polycarbodiimide resin.

(24) The electrical double-layer capacitor of (22) above which is characterized in that the carbonaceous material is prepared by carbonizing a phenolic resin or polycarbodiimide resin, then activating the carbonized resin.

(25) An electrolyte solution for electrical storage devices which is characterized by being composed of the liquid electrolyte for electrical storage devices of (15) or (16) above and an ion-conductive salt which is solid at ambient temperature.

(26) The electrolyte solution for electrical storage devices of (25) above which is characterized in that the ion-conductive salt is a lithium salt.

(27) The electrolyte solution for electrical storage devices of (25) or (26) above which is characterized by including also a nonaqueous organic solvent.

(28) A secondary battery having a positive electrode and a negative electrode, a separator between the positive and negative electrodes, and an electrolyte solution, which secondary battery is characterized in that the electrolyte solution is an electrolyte solution for electrical storage devices according to any one of (25) to (27) above.

(29) An electrical double-layer capacitor having a pair of polarizable electrodes, a separator between the polarizable electrodes and a liquid electrolyte, which electrical double-layer capacitor is characterized in that the liquid electrolyte is an electrolyte solution for electrical storage devices according to any one of (25) to (27) above.

(30) An electrical storage device having a positive electrode and a negative electrode, a separator between the positive and negative electrodes, and a liquid electrolyte, which electrical storage device is characterized in that the positive electrode is activated carbon, the negative electrode is a carbonaceous material that is capable of occluding and releasing lithium ions, and the liquid electrolyte is an electrolyte solution for electrical storage devices according to any one of (25) to (27) above.

BRIEF DESCRIPTION OF THE DIAGRAMS

FIG. 1 is a chart showing the NMR spectrum for compound (3).
FIG. 2 is a chart showing the NMR spectrum for compound (4).
FIG. 3 is a chart showing the NMR spectrum for compound (5).
FIG. 4 is a chart showing the NMR spectrum for compound (6).
FIG. 5 is a chart showing the NMR spectrum for compound (8).
FIG. 6 is a chart showing the NMR spectrum for compound (9).
FIG. 7 is a chart showing the NMR spectrum for compound (10).
FIG. 8 is a chart showing the NMR spectrum for compound (11).
FIG. 9 is a graph of discharge capacity (room temperature) versus initial charge/discharge cycles in the electrical double-layer capacitors obtained in Example 8 according to the invention and Comparative Example 3.
FIG. 10 is a graph showing the temperature dependence of the discharge performance in the electrical double-layer capacitors obtained in Example 8 according to the invention and Comparative Example 3.
FIG. 11 is a graph showing the change over time in voltage (room temperature) after initial charging of the electrical double-layer capacitors obtained in Example 8 according to the invention and Comparative Example 3.
FIG. 12 is a graph showing the charge and discharge characteristics of the secondary battery obtained in Example 9 according to the invention.

BEST MODE FOR CARRYING OUT THE INVENTION

The invention is described more fully below.

Electrolyte Salt for Electrical Storage Devices

The inventive electrolyte salts for electrical storage devices are quaternary salts of general formula (1) below

In the formula, $R^1$ to $R^4$ are each independently an alkyl of 1 to 5 carbons or an alkoxyalkyl of the formula R'—O—$(CH_2)_n$—, wherein R' is methyl or ethyl and the letter n is an integer from 1 to 4. Any two from among $R^1$, $R^2$, $R^3$ and $R^4$ may together form a ring. At least one of groups $R^1$ to $R^4$ is an alkoxyalkyl of the above formula. X is a nitrogen or phosphorus atom, and Y is a monovalent anion.

"Electrical storage device," as used in the invention, refers to a device or element which chemically, physically or physicochemically stores electricity. Illustrative examples include devices capable of being charged and discharged, such as capacitors—including electrical double-layer capacitors, and secondary batteries.

Exemplary alkyls having 1 to 5 carbons include methyl, ethyl, propyl, 2-propyl, butyl and pentyl. Exemplary alkoxyalkyl groups of the formula R'—O—(CH$_2$)$_n$— include methoxymethyl, ethoxymethyl, methoxyethyl, ethoxyethyl, methoxypropyl, ethoxypropyl, methoxybutyl and ethoxybutyl.

Exemplary compounds in which two groups from among R$^1$, R$^2$, R$^3$ and R$^4$ together form a ring include, when X is a nitrogen atom, quaternary ammonium salts containing an aziridine, azetidine, pyrrolidine or piperidine ring; and, when X is a phosphorus atom, quaternary phosphonium salts containing a pentamethylenephosphine (phosphorinane) ring.

Quaternary ammonium salts having as a substituent at least one methoxyethyl group in which R' above is methyl and the letter n is 2 are preferred.

Preferred use can also be made of quaternary salts of general formula (2) below having as substituents a methyl group, two ethyl groups and an alkoxyethyl group.

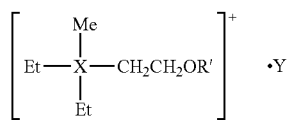

(2)

In formula (2), R' is methyl or ethyl, X is a nitrogen or phosphorus atom, and Y is a monovalent anion. In addition, Me represents a methyl group and Et represents an ethyl group.

No particular limitation is imposed on the monovalent anion Y in general formulas (1) and (2). Illustrative examples include BF$_4^-$, PF$_6^-$, AsF$_6^-$, SbF$_6^-$, AlCl$_4^-$, NbF$_6^-$, HSO$_4^-$, ClO$_4^-$, CH$_3$SO$_3^-$, CF$_3$SO$_3^-$, CF$_3$CO$_2^-$, (CF$_3$SO$_2$)$_2$N$^-$, Cl$^-$, Br$^-$ and I$^-$. From the standpoint of such properties as the degree of dissociation, stability and ion mobility in the non-aqueous organic solvent, the use of BF$_4^-$, PF$_6^-$, (CF$_3$SO$_2$)$_2$N$^-$, CF$_3$SO$_3^-$ or CF$_3$CO$_2^-$ is especially preferred.

Of the quaternary salts of above general formulas (1) and (2), specific examples of quaternary ammonium salts and quaternary phosphonium salts preferred for use in the practice of the invention include compounds (3) to (11) below (wherein Me represents methyl and Et represents ethyl). The quaternary ammonium salts of formulas (3) and (8) below are especially preferred because they enable electrical storage devices having excellent low-temperature characteristics to be obtained.

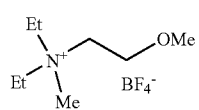

(3)

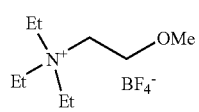

(4)

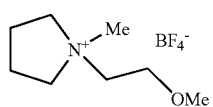

(5)

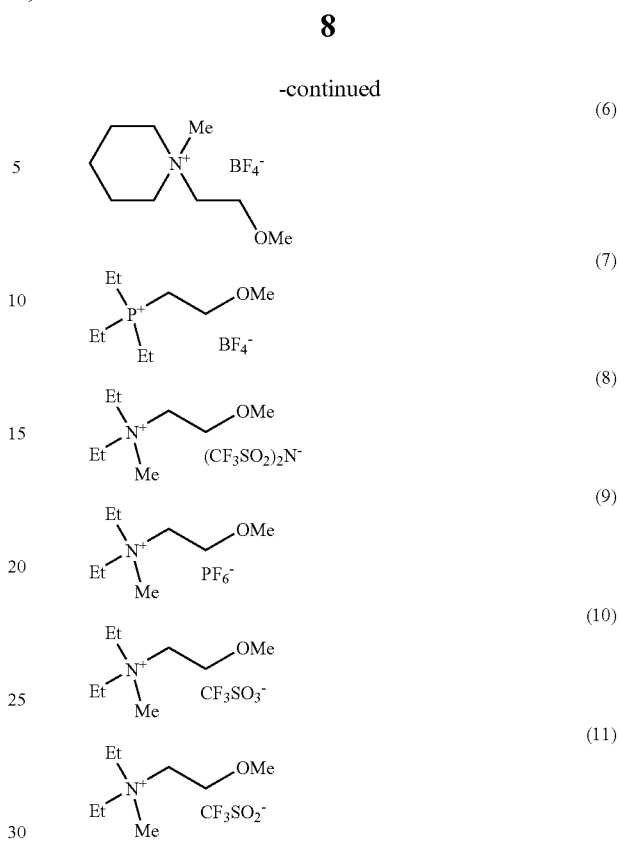

A common method for synthesizing the above quaternary ammonium salts is described. First, a tertiary amine is mixed with a compound such as an alkyl halide or a dialkyl sulfate. If necessary, the mixture is heated, giving a quaternary ammonium halide. Reaction under applied pressure, such as in an autoclave, is preferred when using a compound having low reactivity, such as an alkoxyethyl halide or an alkoxymethyl halide.

The resulting quaternary ammonium halide is dissolved in an aqueous solvent such as water and reacted with a reagent that generates the required anionic species, such as tetrafluoroboric acid or tetrafluorophosphoric acid, to effect an anion exchange reaction, thereby yielding the quaternary ammonium salt of the invention.

In one illustrative method for synthesizing quaternary ammonium tetrafluoroborates, a quaternary ammonium halide is dissolved in water, silver oxide is added and a salt exchange reaction is carried out to form the corresponding quaternary ammonium hydroxide. The product is then reacted with tetrafluoroboric acid, yielding the target compound. This method is effective for synthesizing high-purity quaternary ammonium tetrafluoroborates because the silver halide that forms as a result of salt exchange during formation of the quaternary ammonium hydroxide can easily be removed.

Quaternary phosphonium salts can generally be synthesized in much the same way as quaternary ammonium salts. Typically, a tertiary phosphine is mixed with a suitable compound such as an alkyl halide or a dialkyl sulfate. If necessary, the reaction is carried out under the application of heat.

As in the case of quaternary ammonium salts, quaternary phosphonium salts containing various different anions may be prepared by dissolving a quaternary phosphonium halide (a chloride, bromide or iodide) in an aqueous solvent and reacting the dissolved halide with a reagent that generates the required anionic species so as to effect an anion exchange reaction.

To discourage deposition of the electrolyte salt when an electrolyte solution of the salt dissolved in a nonaqueous organic solvent is placed under low-temperature conditions, it is preferable for the electrolyte salt to have a melting point not higher than 25° C., and preferably not higher than 15° C. An electrolyte salt having a melting point higher than 25° C. deposits out of the solvent at low temperatures, and is thus more likely to lower the ionic conductivity of the electrolyte solution and in turn reduce the amount of electricity that can be drawn from the electrical storage device. The melting point is not subject to any lower limit, although a lower melting point is better.

Ionic Liquid

The ionic liquid according to the present invention is characterized by having general formula (1) below and a melting point of up to 50° C., and preferably up to 25° C.

(1)

In the formula, $R^1$ to $R^4$ are each independently an alkyl of 1 to 5 carbons or an alkoxyalkyl of the formula R'—O—$(CH_2)_n$— (R' being methyl or ethyl and the letter n being an integer from 1 to 4) and any two from among $R^1$, $R^2$, $R^3$ and $R^4$ may together form a ring, with the proviso that at least one of groups $R^1$ to $R^4$ is an alkoxyalkyl of the above formula. X is a nitrogen or phosphorus atom, and Y is a monovalent anion.

Compounds in which two groups from among the alkyls of 1 to 5 carbons $R^1$, $R^2$, $R^3$ and $R^4$ together form a ring are exemplified by the same compounds as mentioned above for electrolyte salts.

In this ionic liquid as well, quaternary ammonium salts having as a substituent at least one methoxymethyl group in which R' above is methyl and the letter n is 2 are preferred.

Preferred use can also be made of quaternary salts of general formula (2) below having as substituents a methyl group, two ethyl groups and an alkoxyethyl group.

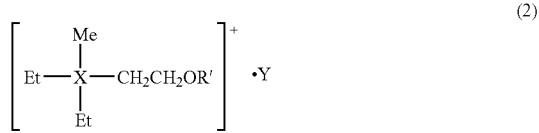

(2)

In the formula, R' is methyl or ethyl, X is a nitrogen or phosphorus atom, and Y is a monovalent anion. In addition, Me represents a methyl group and Et represents an ethyl group.

The monovalent anion Y in the ionic liquid of above general formulas (1) and (2) is exemplified by the same monovalent anions as mentioned above for electrolyte salts.

Specific examples of ionic liquids include compounds of above formulas (3) to (11). The ionic liquids of formulas (3) and (8) are especially preferred because they are easy to handle and they enable electrical storage devices having excellent low-temperature characteristics to be obtained.

The ionic liquid may be prepared in the same way as described above for the electrolyte salt.

The ionic liquids of the invention have numerous desirable features. That is, they (1) have a vapor pressure that is either non-existent or very low, (2) are non-flammable or flame-retarding, (3) have ionic conductivity, (4) have a higher decomposition voltage than water, (5) have a broader liquid temperature range than water, (6) can be handled in air, and (7) have a broader potential window than organic ionic liquids known to the prior art. In particular, when an ionic liquid is used in an electrical storage device, if the potential window is narrow, the electrolyte or electrolyte solution may undergo oxidative decomposition or reductive decomposition. Imidazolium-type ionic liquids have a narrow potential window, and so cannot be used in lithium ion secondary battery systems. However, as noted above, the ionic liquids of this invention have a broad potential window, enabling them to be used in lithium ion secondary batteries as well.

Accordingly, the inventive ionic liquids can be advantageously used as novel electrolytes capable of functioning at temperatures below room temperature in the electrodeposition of metals and alloys, in electroplating baths, and in electrochemical devices for storing energy, such as various types of batteries and capacitors.

Most reaction solvents that are widely used in organic synthesis, such as benzene, methylene chloride and ether, are volatile substances having carcinogenicity. Yet, the ionic liquids of this invention have very low volatilities and also lend themselves well to use as repeatedly reusable reaction solvents for organic synthesis. Hence, they are capable of contributing also to the field of "green chemistry" which is developing new synthetic processes that are less burdensome on the environment.

Liquid Electrolyte for Electrical Storage Devices

The inventive liquid electrolytes for electrical storage devices may be used in any of the following forms: (1) liquid electrolytes consisting solely of the above-described ionic liquids or low-melting electrolyte salts for electrical storage devices (i.e., liquid electrolytes in which a nonaqueous organic solvent is not used), (2) electrolyte solutions obtained by adding an ion-conductive salt to above liquid electrolyte (1) (here too, a nonaqueous organic solvent is not used in the liquid electrolyte), (3) electrolyte solutions obtained by adding also a nonaqueous organic solvent to above electrolyte solution (2), and (4) electrolyte solutions containing at least one of the above-described ionic liquids or electrolytes for electrical storage devices in combination with a nonaqueous organic solvent.

Any nonaqueous organic solvent which is capable of dissolving the above-described ionic liquid or electrolyte salt and is stable within the working voltage range for electrical storage devices such as secondary batteries and electrical double-layer capacitors may be used without particular limitation. However, it is preferable for the nonaqueous organic solvent to be one having a large dielectric constant, a broad electrochemical stability range, a broad service temperature range and excellent safety.

Illustrative examples of suitable solvents include acyclic ethers such as dibutyl ether, 1,2-dimethoxyethane, 1,2-ethoxymethoxyethane, methyl diglyme, methyl triglyme, methyl tetraglyme, ethyl glyme, ethyl diglyme, butyl diglyme, and glycol ethers (e.g., ethyl cellosolve, ethyl carbitol, butyl cellosolve, butyl carbitol); cyclic ethers such as tetrahydrofuran, 2-methyltetrahydrofuran, 1,3-dioxolane and 4,4-dimethyl-1,3-dioxane; butyrolactones such as γ-butyrolactone, γ-valerolactone, δ-valerolactone, 3-methyl-1,3- oxazolidin-2-one and 3-ethyl-1,3-oxazolidin-2-one; and solvents commonly used in electrochemical devices, such as amide solvents (e.g., N-methylformamide, N,N-dimethylformamide, N-methylacetamide, N-methylpyrrolidinone), carbonate solvents (e.g., diethyl carbonate, dimethyl carbonate, ethyl methyl carbonate, propylene carbonate, ethylene carbonate, styrene carbonate), and imidazolidinone solvents (e.g., 1,3-dimethyl-2-imidazolidinone). Any one or mixtures of two or more of these solvents may be used.

The use of a mixed solvent which includes as a main component ethylene carbonate or propylene carbonate, or of one or a mixture of two or more solvents selected from among ethylene carbonate, propylene carbonate, vinylene carbonate, dimethyl carbonate, ethyl methyl carbonate and diethyl carbonate, is preferred.

When the above-described liquid electrolyte is used as a liquid electrolyte for electrical storage devices, in the form described in (1) above it is of course 100% ionic liquid. In above forms (2), (3) and (4), the concentration of ionic liquid or electrolyte salt in the solvent, while not subject to any particular limitation, is generally 0.1 to 5.0 mol/L, and preferably 1.0 to 4.0 mol/L. At a concentration of less than 0.1 mol/L, energy loss may rise due to increased internal resistance. On the other hand, at a concentration higher than 5.0 mol/L, if the electrolyte salt has a low solubility and a relatively high melting point, undesirable effects may arise at low temperatures, such as deposition of the salt and a decline in stability.

Because the electrolyte salts for electrical storage devices of the invention have a better solubility in nonaqueous organic solvents than conventional electrolyte salts and have a melting point no higher than 25° C., the electrolyte salt does not readily deposit out of solution at low temperatures even when used at a higher electrolyte salt concentration than is normally the practice.

As noted above, an ion-conductive salt may be added to the liquid electrolyte.

In this case, the ion-conductive salt may be any that is capable of being used in electrical storage devices, such as lithium secondary cells, lithium ion secondary cells and electrical double-layer capacitors. Ion-conductive salts that may be used include alkali metal salts and quaternary ammonium salts.

Preferred alkali metal salts are lithium salts, sodium salts and potassium salts. Specific examples include: (1) lithium salts such as lithium tetrafluoroborate, lithium hexafluorophosphate, lithium perchlorate, lithium trifluoromethanesulfonate, the sulfonyl imide lithium salts of general formula (12) below, the sulfonyl methide lithium salts of general formula (13) below, lithium acetate, lithium trifluoroacetate, lithium benzoate, lithium p-toluenesulfonate, lithium nitrate, lithium bromide, lithium iodide and lithium tetraphenylborate; (2) sodium salts such as sodium perchlorate, sodium iodide, sodium tetrafluoroborate, sodium hexafluorophosphate, sodium trifluoromethanesulfonate and sodium bromide; and (3) potassium salts such as potassium iodide, potassium tetrafluoroborate, potassium hexafluorophosphate and potassium trifluoromethanesulfonate.

$(R^a\text{—}SO_2)(R^b\text{—}SO_2)NLi$ (12)

$(R^c\text{—}SO_2)(R^d\text{—}SO_2)(R^e\text{—}SO_2)CLi$ (13)

In above formulas (12) and (13), $R^a$ to $R^e$ are each independently $C_{1-4}$ perfluoroalkyl groups which may have one or two ether linkages.

Illustrative examples of the sulfonyl imide lithium salts of general formula (12) include $(CF_3SO_2)_2NLi$, $(C_2F_5SO_2)_2NLi$, $(C_3F_7SO_2)_2NLi$, $(C_4F_9SO_2)_2NLi$, $(CF_3SO_2)(C_2F_5SO_2)NLi$, $(CF_3SO_2)(C_3F_7SO_2)NLi$, $(CF_3SO_2)(C_4F_9SO_2)NLi$, $(C_2F_5SO_2)(C_3F_7SO_2)NLi$, $(C_2F_5SO_2)(C_4F_9SO_2)NLi$ and $(CF_3OCF_2SO_2)_2NLi$.

Illustrative examples of the sulfonyl methide lithium salts of general formula (13) include $(CF_3SO_2)_3CLi$, $(C_2F_5SO_2)_3CLi$, $(C_3F_7SO_2)_3CLi$, $(C_4F_9SO_2)_3CLi$, $(CF_3SO_2)_2(C_2F_5SO_2)CLi$, $(CF_3SO_2)_2(C_3F_7SO_2)CLi$, $(CF_3SO_2)_2(C_4F_9SO_2)CLi$, $(CF_3SO_2)(C_2F_5SO_2)_2CLi$, $(CF_3SO_2)(C_3F_7SO_2)_2CLi$, $(CF_3SO_2)(C_4F_9SO_2)_2CLi$, $(C_2F_5SO_2)_2(C_3F_7SO_2)CLi$, $(C_2F_5SO_2)_2(C_4F_9SO_2)CLi$ and $(CF_3OCF_2SO_2)_3CLi$.

Of the above, lithium tetrafluoroborate, lithium hexafluorophosphate, sulfonyl methide lithium salts of general formula (12) and general formula (13) are preferred because they are ion-conductive salts having a particularly high ionic conductivity and excellent thermal stability. These ion-conductive salts may be used singly or as combinations of two or more thereof.

Quaternary ammonium salts that may be used in electrical double-layer capacitors include tetramethylammonium hexafluorophosphate, tetraethylammonium hexafluorophosphate, tetrapropylammonium hexafluorophosphate, methyltriethylammonium hexafluorophosphate, tetraethylammonium tetrafluoroborate and tetraethylammonium perchlorate; and also acylic amidines, cyclic amidines (e.g., imidazoles, imidazolines, pyrimidines, 1,5-diazabicyclo[4.3.0]non-5-ene (DBN), 1,8-diazabicyclo[5.4.0]undec-7-ene (DBU)), pyrroles, pyrazoles, oxazoles, thiazoles, oxadiazoles, thiadiazoles, triazoles, pyridines, pyrazines, triazines, pyrrolidines, morpholines, piperidines and piperazines.

The ion-conductive salt has a concentration in the electrolyte solution of generally 0.05 to 3 mol/L, and preferably 0.1 to 2 mol/L. Too low an ion-conductive salt concentration may make it impossible to obtain a sufficient ionic conductivity, whereas too high a concentration may prevent complete dissolution in the liquid electrolyte.

Electrical Double-Layer Capacitor

The electrical double-layer capacitor of the invention is composed of a pair of polarizable electrodes, a separator between the polarizable electrodes, and a liquid electrolyte, the latter being a liquid electrolyte of the type described above for use in electrical storage devices.

The polarizable electrodes may be ones produced by coating a current collector with a polarizable electrode composition containing a carbonaceous material and a binder polymer.

The carbonaceous material is not subject to any particular limitation. Illustrative examples include carbonaceous materials prepared by the carbonization of a suitable starting material, or by both carbonization and subsequent activation of the carbonized material to yield activated carbon. Examples of suitable starting materials include plant-based materials such as wood, sawdust, coconut shells and pulp spent liquor; fossil fuel-based materials such as coal and petroleum fuel oil, as well as fibers spun from coal or petroleum pitch obtained by the thermal cracking of such fossil fuel-based materials or from tar pitch; and synthetic polymers, phenolic resins, furan resins, polyvinyl chloride resins, polyvinylidene chloride resins, polyimide resins, polyamide resins, polycarbodiimide resins, liquid-crystal polymers, plastic waste and reclaimed tire rubber.

Of the above, to prevent a decline in performance due to variability of the starting material or impurities in the starting material, it is preferable for the carbonaceous material to be composed primarily of a resin-derived carbonaceous material. A carbonaceous material obtained by the carbonization of a phenolic resin or polycarbodiimide resin, followed by activation is especially preferred.

Any known type of phenolic resin may be used without particular limitation. Illustrative examples include resole-type resins, novolak resins, and other special phenolic resins.

Polycarbodiimide resins obtained by any of various known processes may likewise be used without particular limitation (see U.S. Pat. No. 2,941,966, JP-B 47-33279, *J. Org. Chem.* 20, 2069-2075 (1963), etc.). For example, use may be made of a polycarbodiimide resin prepared by the decarboxylative condensation of an organic diisocyanate.

The method of activation is not subject to any particular limitation. Examples of such techniques that may be used include chemical activation and steam activation. Activated carbon prepared by chemical activation using KOH is preferred because the resulting capacitor tends to have a larger electrostatic capacitance than when steam-activated carbon is used.

The carbonaceous material used in the practice of the invention may be in any of various forms, including shredded material, granulated material, pellets, fibers, felt, woven fabric or sheet.

A conductive material may be added to the carbonaceous material. Any conductive material capable of imparting conductivity to the carbonaceous material may be used without particular limitation. Illustrative examples include carbon black, Ketjenblack, acetylene black, carbon whiskers, carbon fibers, natural graphite, synthetic graphite, titanium oxide, ruthenium oxide, and metallic fibers such as aluminum and nickel. Any one or combinations of two or more of the above may be used. The use of Ketjenblack, which is a type of carbon black, or acetylene black is preferred.

No particular limitation is imposed on the average particle size of the conductive material, although it is desirable for the conductive material to have an average particle size of preferably 10 nm to 10 µm, more preferably 10 to 100 nm, and most preferably 20 to 40 nm. In particular, it is advantageous for the conductive material to have an average particle size within a range of 1/5000 to 1/2, and especially 1/1000 to 1/10, the average particle size of the carbonaceous material.

The amount of addition is not subject to any particular limitation. However, to achieve a good electrostatic capacitance and a good conductivity imparting effect, addition in an amount of 0.1 to 20 parts by weight, and especially 0.5 to 10 parts by weight, per 100 parts by weight of the carbonaceous material is preferred.

The binder polymer may be any polymer suitable for use in the present application. Preferred examples include (I) unsaturated polyurethane compounds; (II) polymeric materials having an interpenetrating network structure or a semi-interpenetrating network structure; (III) thermoplastic resins containing units of general formula (14) below; and (IV) fluoropolymer materials. The use of any of polymeric materials (I) to (III) results in a high adhesion, and can therefore increase the physical strength of the electrodes. As for fluoropolymer materials (IV), these have excellent thermal and electrical stability.

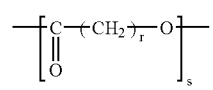  (14)

In the formula, the letter r is an integer from 3 to 5 and the letter s is an integer which is 5 or higher.

The above-described unsaturated polyurethane compounds (I) are preferably ones prepared by reacting (A) an unsaturated alcohol having at least one (meth)acryloyl group and a hydroxyl group on the molecule, (B) a polyol compound of general formula (15) below, (C) a polyisocyanate compound, and (D) an optional chain extender.

  (15)

In the formula, $R^5$ and $R^6$ are each independently a divalent hydrocarbon group of 1 to 10 carbons which may contain an amino, nitro, carbonyl or ether group; Z is —COO—, —OCOO—, —NR$^7$CO— ($R^7$ being a hydrogen atom or an alkyl group of 1 to 4 carbons), —O— or an arylene group; the letters h, i and j are each independently 0 or an integer from 1 to 10; and the letter q is an integer which is 1 or higher.

The unsaturated alcohol serving as component (A) is not subject to any particular limitation, provided the molecule bears at least one (meth)acryloyl group and a hydroxyl group. Illustrative examples include 2-hydroxyethyl acrylate, 2-hydroxypropyl acrylate, 2-hydroxyethyl methacrylate, 2-hydroxypropyl methacrylate, diethylene glycol monoacrylate, diethylene glycol monomethacrylate, triethylene glycol monoacrylate and triethylene glycol monomethacrylate.

The polyol compound serving as component (B) may be, for example, a polyether polyol such as polyethylene glycol or a polyester polyol such as polycaprolactone. A polyol compound of general formula (15) above is especially preferred.

In above formula (15), $R^5$ and $R^6$ are each independently a divalent hydrocarbon group of 1 to 10 carbons, and preferably 1 to 6 carbons, which may contain an amino, nitro, carbonyl or ether group. Preferred examples include alkylene groups such as methylene, ethylene, trimethylene, propylene, ethylene oxide and propylene oxide groups.

The letter q is a number which is ≧1, preferably ≧5, and most preferably from 10 to 200.

The polyol compound serving as component (B) has a number-average molecular weight of preferably 400 to 10,000, and more preferably 1,000 to 5,000.

Illustrative examples of the polyisocyanate compound serving as component (C) include aromatic diisocyanates such as tolylene diisocyanate, 4,4'-diphenylmethane diisocyanate, p-phenylene diisocyanate, 1,5-naphthylene diisocyanate, 3,3'-dichloro-4,4'-diphenylmethane diisocyanate and xylylene diisocyanate; and aliphatic or alicyclic diisocyanates such as hexamethylene diisocyanate, isophorone diisocyanate, 4,4'-dichlorohexylmethane diisocyanate and hydrogenated xylylene diisocyanate.

The above polyurethane compound is preferably one prepared from above components (A) to (C) and also a chain extender (D). Any chain extender commonly used in the preparation of thermoplastic polyurethane resins may be employed. Illustrative examples include glycols such as ethylene glycol and diethylene glycol; aliphatic diols such as 1,3-propanediol and 1,4-butanediol; aromatic or alicyclic diols such as 1,4-bis(β-hydroxyethoxy)benzene, 1,4-cyclohexanediol and xylylene glycol; diamines such as hydrazine, ethylenediamine, hexamethylenediamine, xylylenediamine and piperazine; and amino alcohols such as adipoyl hydrazide and isophthaloyl hydrazide. Any one or combinations of two or more of these may be used.

Use may also be made of a urethane prepolymer prepared by the preliminary reaction of the polyol compound serving as component (B) with the polyisocyanate compound serving as component (C).

It is advantageous to use components (A) to (D) in the following proportions:
(A) 100 parts by weight;
(B) 100 to 20,000 parts by weight, and preferably 1,000 to 10,000 parts by weight;
(C) 80 to 5,000 parts by weight, and preferably 300 to 2,000 parts by weight; and optionally,
(D) 5 to 1,000 parts by weight, and preferably 10 to 500 parts by weight.

The resulting unsaturated polyurethane compound has a number-average molecular weight of preferably 1,000 to 50,000, and most preferably 3,000 to 30,000. Too small a number-average molecular weight results in a small molecular weight between crosslink sites in the cured gel, which may give it insufficient flexibility as a binder polymer. On the other hand, a number-average molecular weight that is too large may cause the viscosity of the electrode composition prior to curing to become so large as to make it difficult to fabricate an electrode having a uniform coat thickness.

The above-mentioned polymeric material having an interpenetrating network structure or semi-interpenetrating network structure (II) may be composed of two or more compounds, such as polymers or reactive monomers, which are capable of forming a mutually interpenetrating or semi-interpenetrating network structure.

Examples of such polymeric materials and the two or more compounds of which they are composed include:
(A) a polymer matrix formed by combining (a) a hydroxyalkyl polysaccharide derivative with (d) a crosslinkable functional group-bearing compound;
(B) a polymer matrix formed by combining (b) a polyvinyl alcohol derivative with (d) a crosslinkable functional group-bearing compound; and
(C) a polymer matrix formed by combining (c) a polyglycidol derivative with (d) a crosslinkable functional group-bearing compound.

Use of the above-described unsaturated polyurethane compound (I) as part or all of the crosslinkable functional group-bearing compound (d) is advantageous for improving physical strength and other reasons.

Any of the following may be used as the hydroxyalkyl polysaccharide derivative serving as component (a):
(1) hydroxyethyl polysaccharides prepared by reacting ethylene oxide with a naturally occurring polysaccharide such as cellulose, starch or pullulan,
(2) hydroxypropyl polysaccharides prepared by reacting propylene oxide with the above naturally occurring polysaccharide,
(3) dihydroxypropyl polysaccharides prepared by reacting glycidol or 3-chloro-1,2-propanediol with the above naturally occurring polysaccharide.

Some or all of the hydroxyl groups on these hydroxyalkyl polysaccharides may be capped with an ester-bonded or ether-bonded substituent.

The above hydroxyalkyl polysaccharides have a molar degree of substitution of 2 to 30, and preferably 2 to 20. At a molar substitution below 2, the ability of the hydroxyalkyl polysaccharide to solvate electrolyte salts becomes so low as to make the hydroxyalkyl polysaccharide unsuitable for use.

The hydroxyalkyl polysaccharide derivative in which some or all of the hydroxyl groups have been capped with ester-bonded or ether-bonded substituents may be one in which at least 10% of the terminal OH groups on the molecular chains have been capped with one or more type of monovalent group selected from among halogen atoms, substituted or unsubstituted monovalent hydrocarbon groups, $R^8CO$— groups (wherein $R^8$ is a substituted or unsubstituted monovalent hydrocarbon group), $R^8_3Si$— groups (wherein $R^8$ is the same as above), amino groups, alkylamino groups, $H(OR^9)_m$— groups (wherein $R^9$ is an alkylene group of 2 to 5 carbons and the letter m is an integer from 1 to 100), and phosphorus-containing groups.

The substituted or unsubstituted monovalent hydrocarbon groups are like or unlike monovalent hydrocarbon groups having 1 to 10 carbons, and preferably 1 to 8 carbons. Illustrative examples include alkyls such as methyl, ethyl, propyl, isopropyl, t-butyl and pentyl; aryls such as phenyl and tolyl; aralkyls such as benzyl; alkenyls such as vinyl; and any of the foregoing groups in which some or all of the hydrogen atoms have been substituted with halogen, cyano, hydroxyl, amino or other substituents. Any one or combinations of two or more such groups may be used.

The polyvinyl alcohol derivative serving as component (b) is a polymeric compound having oxyalkylene chain-bearing polyvinyl alcohol units in which some or all of the hydroxyl groups are substituted. Here, "hydroxyl groups" refers collectively to residual hydroxyl groups originating from the polyvinyl alcohol units and hydroxyl groups on the oxyalkylene-containing groups that have been introduced onto the molecule.

The polymeric compound having polyvinyl alcohol units has an average degree of polymerization of at least 20, preferably at least 30, and most preferably at least 50. Some or all of the hydroxyl groups on the polyvinyl alcohol units are substituted with oxyalkylene-containing groups. For ease of handling and other reasons, the upper limit in the number-average degree of polymerization is preferably not higher than 2,000, more preferably not higher than 500, and most preferably not higher than 200.

It is most advantageous for the polyvinyl alcohol unit-containing polymeric compound to be a homopolymer which satisfies the above range in the number-average degree of polymerization and in which the fraction of polyvinyl alcohol units within the molecule is at least 98 mol %. However, use can also be made of polyvinyl alcohol unit-containing polymeric compounds which satisfy the above range in the number-average degree of polymerization and have a polyvinyl alcohol fraction of preferably at least 60 mol %, and more preferably at least 70 mol %. Illustrative examples include polyvinylformal in which some of the hydroxyl groups on the polyvinyl alcohol have been converted to formal, modified polyvinyl alcohols in which some of the hydroxyl groups on the polyvinyl alcohol have been alkylated, poly(ethylene vinyl alcohol), partially saponified polyvinyl acetate, and other modified polyvinyl alcohols.

Some or all of the hydroxyl groups on the polyvinyl alcohol units of the polymeric compound are substituted with oxyalkylene-containing groups (moreover, some of the hydrogen atoms on these oxyalkylene groups may be substituted with hydroxyl groups) to an average molar substitution of at least 0.3. The proportion of hydroxyl groups substituted with oxyalkylene-containing groups is preferably at least 30 mol %, and more preferably at least 50 mol %. The average molar substitution (MS) can be determined by accurately measuring the weight of the polyvinyl alcohol charged and the weight of the reaction product.

The polyglycidol derivative serving as component (c) is a compound containing units of formula (16) below (referred to hereinafter as "A units")

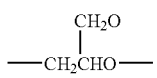

(16)

and units of formula (17) (referred to hereinafter as "B units")

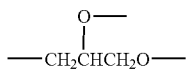

(17)

The ends of the molecular chains on the compound are capped with specific substituents.

The polyglycidol can be prepared by polymerizing glycidol or 3-chloro-1,2-propanediol, although it is generally advisable to carry out polymerization using glycidol as the starting material, and using a basic catalyst or a Lewis acid catalyst.

The total number of A and B units on the polyglycidol molecule is preferably at least two, more preferably at least six, and most preferably at least ten. There is no particular upper limit, although the total number of such groups generally is not more than about 10,000. The total number of these units may be set as appropriate for the required flowability, viscosity and other properties of the polyglycidol. The ratio of A units to B units (A:B) in the molecule is within a range of preferably 1/9 to 9/1, and especially 3/7 to 7/3. The A and B units do not appear in a regular order, and may be arranged in any combination.

The polyglycidol has a polyethylene glycol equivalent weight-average molecular weight (Mw), as determined by gel permeation chromatography (GPC), within a range of preferably 200 to 730,000, more preferably 200 to 100,000, and most preferably 600 to 20,000. The polydispersity (Mw/Mn) is preferably 1.1 to 20, and most preferably 1.1 to 10.

The polyglycidol in which the molecular chains are end-capped with substituents is a polyglycidol derivative in which at least 10% of the terminal hydroxyl groups on the molecular chains are capped with one or more type of monovalent group selected from among halogen atoms, substituted or unsubstituted monovalent hydrocarbon groups, $R^{10}CO-$ groups of 1 to 10 carbons (wherein $R^{10}$ is a substituted or unsubstituted monovalent hydrocarbon group), $R^{10}{}_3Si-$ groups (wherein $R^{10}$ is as defined above), amino groups, alkylamino groups, $H(OR^{11})_u-$ groups (wherein $R^{11}$ is an alkylene group of 2 to 5 carbons, and the letter u is an integer from 1 to 100), and phosphorus atom-containing groups.

The foregoing substituted or unsubstituted monovalent hydrocarbon groups of 1 to 10 carbons are exemplified by the same groups as those mentioned above for $R^8$ and $R^9$. Such groups having 1 to 8 carbons are especially preferred. Substitution may be carried out by using known techniques for introducing various substituents at hydroxyl end groups.

Any of the following may be used as the crosslinkable functional group-bearing compound serving as component (d):

(1) an epoxy group-bearing compound in combination with a compound having two or more active hydrogens capable of reacting with the epoxy group;
(2) an isocyanate group-bearing compound in combination with a compound having two or more active hydrogens capable of reacting with the isocyanate group;
(3) a compound having two or more reactive double bonds.

Preferred examples of the epoxy group-bearing compound (1) include compounds having two or more epoxy groups on the molecule, such as sorbitol polyglycidyl ether, sorbitan polyglycidyl ether, polyglycerol polyglycidyl ether, pentaerythritol polyglycidyl ether, diglycerol polyglycidyl ether and triglycidyl tris(2-hydroxyethyl) isocyanurate.

A three-dimensional network structure can be formed by reacting the above epoxy group-bearing compound with a compound having at least two active hydrogens, such as an amine, alcohol, carboxylic acid or phenol. Illustrative examples include polymeric polyols such as polyethylene glycol, polypropylene glycol and ethylene glycol-propylene glycol copolymers, and also ethylene glycol, 1,2-propylene glycol, 1,3-propylene glycol, 1,3-butanediol, 1,4-butanediol, 1,5-pentanediol, 2,2-dimethyl-1,3-propanediol, diethylene glycol, dipropylene glycol, 1,4-cyclohexanedimethanol, 1,4-bis(β-hydroxyethoxy)benzene, and p-xylylenediol; polyamines such as phenyl diethanolamine, methyl diethanolamine and polyethyleneimine; and polycarboxylic acids.

Illustrative examples of the isocyanate group-bearing compound (2) include compounds having two or more isocyanate groups, such as tolylene diisocyanate, xylylene diisocyanate, naphthylene diisocyanate, diphenylmethane diisocyanate, biphenylene diisocyanate, diphenyl ether diisocyanate, tolidine diisocyanate, hexamethylene diisocyanate and isophorone diisocyanate.

An isocyanato-terminal polyol compound prepared by reacting the above isocyanate compound with a polyol compound can also be used.

In this case, the stoichiometric ratio between the isocyanate groups [NCO] on the isocyanate compound and the hydroxyl groups [OH] on the polyol compound is such as to satisfy the condition [NCO]>[OH]. The ratio [NCO]/[OH] is preferably in a range of 1.03/1 to 10/1, and especially 1.10/1 to 5/1.

Alternatively, instead of the polyol, an amine having two or more active hydrogens may be reacted with the isocyanate. The amine used may be one having a primary or a secondary amino group, although a primary amino group-bearing compound is preferred. Suitable examples include diamines such as ethylenediamine, 1,6-diaminohexane, 1,4-diaminobutane and piperazine; polyamines such as polyethyleneamine; and amino alcohols such as N-methyldiethanolamine and aminoethanol. Of these, diamines in which the functional groups have the same level of reactivity are especially preferred. Here too, the stoichiometric ratio between [NCO] groups on the isocyanate compound and [NH$_2$] or [NH] groups on the amine compound is such as to satisfy the condition [NCO]>[NH$_2$]+[NH].

The above isocyanate group-bearing compounds cannot by themselves form three-dimensional network structures. However, three-dimensional network structures can be formed by reacting the isocyanate group-bearing compound with a compound having at least two active hydrogens, such as an amine, alcohol, carboxylic acid or phenol.

Suitable compounds having two or more active hydrogens are exemplified by the same compounds as those mentioned above.

The aforementioned reactive double bond-bearing compound (3) is not subject to any particular limitation, although preferred examples include the above-described unsaturated polyurethane compounds (I) and polyoxyalkylene component-bearing diesters of general formula (18) below. The use of these in combination with a polyoxyalkylene component-bearing monoester of general formula (19) below and a triester is recommended.

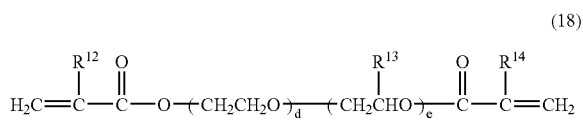

In formula (18), $R^{12}$, $R^{13}$ and $R^{14}$ are each independently a hydrogen atom or an alkyl group having 1 to 6 carbons, and preferably 1 to 4 carbons, such as methyl, ethyl, n-propyl, i-propyl, n-butyl, i-butyl, s-butyl and t-butyl; and the letters d and e satisfy the condition $d \geqq 1$ and $e \geqq 0$ or the condition $d \geqq 0$ and $e \geqq 1$. The sum d+e is preferably no higher than 100, and especially from 1 to 30. $R^{12}$, $R^{13}$ and $R^{14}$ are most preferably methyl, ethyl, n-propyl, i-propyl, n-butyl, i-butyl, s-butyl or t-butyl.

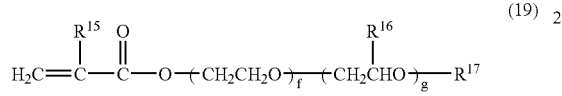

In formula (19), $R^{15}$, $R^{16}$ and $R^{17}$ are each independently a hydrogen atom or an alkyl group having 1 to 6 carbons, and preferably 1 to 4 carbons, such as methyl, ethyl, n-propyl, i-propyl, n-butyl, i-butyl, s-butyl and t-butyl; and the letters f and g satisfy the condition $f \geqq 1$ and $g \geqq 0$ or the condition $f \geqq 0$ and $g \geqq 1$. The sum f+g is preferably no higher than 100, and especially from 1 to 30. $R^{15}$, $R^{16}$ and $R^{17}$ are most preferably methyl, ethyl, n-propyl, i-propyl, n-butyl, i-butyl, s-butyl or t-butyl.

If necessary, a compound containing an acrylic or methacrylic group may be added. Examples of such compounds include acrylates and methacrylates such as glycidyl methacrylate, glycidyl acrylate and tetrahydrofurfuryl methacrylate, as well as methacryloyl isocyanate, 2-hydroxymethylmethacrylic acid and N,N-dimethylaminoethylmethacrylic acid. Other reactive double bond-containing compounds may be added as well, such as acrylamides (e.g., N-methylolacrylamide, methylenebisacrylamide, diacetoneacrylamide), and vinyl compounds such as vinyloxazolines and vinylene carbonate.

Here too, in order to form a three-dimensional network structure, a compound having at least two reactive double bonds like those mentioned above must be added.

Typically, the above-described unsaturated polyurethane compound (I) or polyoxyalkylene component-bearing diester compound and the polyoxyalkylene component-bearing monoester compound are heated or exposed to a suitable form of radiation, such as electron beams, microwaves or radiofrequency radiation, within the electrode composition, or a mixture of the compounds is heated, so as to form the three-dimensional network structure.

The addition of a polyoxyalkylene component-bearing monoester compound, which is a monofunctional monomer, to the unsaturated polyurethane compound or the polyoxyalkylene component-bearing diester compound is desirable because such addition introduces polyoxyalkylene branched chains onto the three-dimensional network.

No particular limitation is imposed on the relative proportions of the unsaturated polyurethane compound or polyoxyalkylene component-bearing diester compound and the polyoxyalkylene component-bearing monoester compound.

The binder polymer containing component (a), (b) or (c) in combination with component (d), when heated or exposed to a suitable form of radiation, such as electron beams, microwaves or radio-frequency radiation, forms a semi-interpenetrating polymer network structure in which molecular chains of a polymer of component (a), (b) or (c) are interlocked with the three-dimensional network structure of a polymer formed by the reaction (polymerization) of the crosslinkable functional group-bearing compound serving as component (d).

Thermoplastic resins containing units of general formula (14) below may be used as the above-mentioned type (III) binder polymer.

In the formula, the letter r is 3, 4 or 5, and the letter s is an integer $\geqq 5$.

Such a thermoplastic resin is preferably a thermoplastic polyurethane resin prepared by reacting (E) a polyol compound with (F) a polyisocyanate compound and (G) a chain extender.

Suitable thermoplastic polyurethane resins include not only polyurethane resins having urethane linkages, but also polyurethane-urea resins having both urethane linkages and urea linkages.

Preferred examples of the polyol compound serving as component (E) above include polyester polyol, polyester polyether polyol, polyester polycarbonate polyol, polycaprolactone polyol, and mixtures thereof.

The polyol compound serving as component (E) has a number-average molecular weight of preferably 1,000 to 5,000, and most preferably 1,500 to 3,000. A polyol compound having too small a number-average molecular weight may lower the physical properties of the resulting thermoplastic polyurethane resin film, such as the heat resistance and tensile elongation. On the other hand, too large a number-average molecular weight increases the viscosity during synthesis, which may lower the production stability of the thermoplastic polyurethane resin being prepared. The number-average molecular weights used here in connection with polyol compounds are calculated based on the hydroxyl values measured in accordance with JIS K1577.

Illustrative examples of the polyisocyanate compound serving as above component (F) include aromatic diisocyanates such as tolylene diisocyanate, 4,4'-diphenylmethane diisocyanate, p-phenylene diisocyanate, 1,5-naphthylene diisocyanate and xylylene diisocyanate; and aliphatic or alicyclic diisocyanates such as hexamethylene diisocyanate, isophorone diisocyanate, 4,4'-dicyclohexylmethane diisocyanate and hydrogenated xylylene diisocyanate.

The chain extender serving as above component (G) is preferably a low-molecular-weight compound having a molecular weight of not more than 300 and bearing two active hydrogen atoms capable of reacting with isocyanate groups.

Various types of known compounds may be used as such low-molecular-weight compounds. Illustrative examples include aliphatic diols such as ethylene glycol, propylene glycol and 1,3-propanediol; aromatic or alicyclic diols such as 1,4-bis(β-hydroxyethoxy)benzene, 1,4-cyclohexanediol and bis(β-hydroxyethyl) terephthalate; diamines such as hydrazine, ethylenediamine, hexamethylenediamine and xylylenediamine; and amino alcohols such as adipoyl hydrazide. Any one or combinations of two or more of these may be used.

In preparing the thermoplastic polyurethane resin, it is advantageous to react the above components in the following proportions:

(E) 100 parts by weight of the polyol compound;
(F) 5 to 200 parts by weight, and preferably 20 to 100 parts by weight, of the polyisocyanate compound;
(G) 1 to 200 parts by weight, and preferably 5 to 100 parts by weight, of the chain extender.

The thermoplastic resin has a swelling ratio, as determined from the formula indicated below, within a range of 150 to 800%, preferably 250 to 500%, and most preferably 250 to 400%.

$$\text{Swelling ratio (\%)} = \frac{\text{weight in grams of swollen thermoplastic resin after 24-hour immersion in electrolyte solution at 20° C. (g)}}{\text{weight in grams of thermoplasic resin before immersion in electrolyte solution at 20° C. (g)}} \times 100$$

Preferred examples of fluoropolymer materials that may be used as the above-mentioned type (IV) binder polymer include polyvinylidene fluoride (PVDF), vinylidene fluoride-hexafluoropropylene copolymers (P(VDF-HFP)) and vinylidene fluoride-chlorotrifluoroethylene copolymers (P(VDF-CTFE)). Of these, fluoropolymers having a vinylidene fluoride content of preferably at least 50 wt %, and most preferably at least 70 wt %, are especially desirable. The upper limit in the vinylidene fluoride content of the fluoropolymer is preferably about 97 wt %.

No particular limitation is imposed on the weight-average molecular weight of the fluoropolymer, although the weight-average molecular weight is preferably from 500,000 to 2,000,000, and most preferably from 500,000 to 1,500,000. Too low a weight-average molecular weight may result in an excessive decline in physical strength.

The polarizable electrode composition can be produced by charging a mixer with a binder solution prepared from the above-described carbonaceous material (which includes, if necessary, a conductive material), a binder polymer and, optionally, a solvent, then wet mixing.

The amount of binder polymer added is preferably 0.5 to 20 parts by weight, and most preferably 1 to 10 parts by weight, per 100 parts by weight of the carbonaceous material.

The polarizable electrode composition prepared as described above is coated onto a current conductor, thereby forming a polarizable electrode. Any positive and negative electrode current collectors commonly used in electrical double-layer capacitors may be selected and used, although the positive electrode current collector is preferably aluminum foil or aluminum oxide and the negative electrode current collector is preferably copper foil, nickel foil, or a metal foil whose surface is formed of a film of plated copper or nickel.

The foils making up the respective current collectors may be in any of various shapes, including thin foils, flat sheets, and perforated, stampable sheets. The foil has a thickness of generally about 1 to 200 μm. For optimal characteristics, such as density of the carbonaceous material as a portion of the overall electrode and electrode strength, a thickness of 8 to 100 μm, and especially 8 to 30 μm, is preferred.

The polarizable electrode can be produced by melting and blending the polarizable electrode composition, then extruding the blend as a film.

The separator referred to above may be of a type that is commonly used in electrical double-layer capacitors. Illustrative examples include (1) separators produced by impregnating a separator base with a liquid electrolyte, (2) separators produced by shaping the polymer binder used in the polarizable electrode as a film, and (3) separators composed of a gel electrolyte film produced by shaping a thermoplastic resin having a swelling ratio, as determined by the formula indicated above, within a range of 150 to 800%, then impregnating the resin with a liquid electrolyte so as to induce it to swell. The liquid electrolyte used for this purpose may be any of the various types of above-mentioned liquid electrolytes for electrical storage devices.

The separator base used in type (1) separators may be one that is commonly used in electrical double-layer capacitors. Illustrative examples include polyolefin nonwoven fabric, polytetrafluoroethylene porous film, kraft paper, sheet laid from a blend of rayon fibers and sisal fibers, manila hemp sheet, glass fiber sheet, cellulose-based electrolytic paper, paper made from rayon fibers, paper made from a blend of cellulose and glass fibers, and combinations thereof in the form of multilayer sheets.

Other types of separators that may be used include (2) separators produced by shaping the polymer binder used in the polarizable electrodes as a film, and (3) separators composed of a gel electrolyte film obtained by shaping a thermoplastic resin having a swelling ratio, as determined by the formula indicated above, within a range of 150 to 800%, then impregnating the resin with a liquid electrolyte so as to induce it to swell.

Because such separators have the same composition as the polymer binder (thermoplastic resin) used in the electrodes, the electrode/separator interface can be integrally united and controlled, making it possible to further lower the internal resistance of the capacitor.

The electrical double-layer capacitor of the invention can be assembled by stacking, fan-folding or winding an electrical double-layer capacitor assembly composed of a pair of polarizable electrodes produced as described above and a separator therebetween. The cell assembly is formed into a coin-like shape, then placed within a capacitor housing such as a can or a laminate pack. The assembly is then filled with the liquid electrolyte, following which the housing is mechanically sealed if it is a can or heat-sealed if it is a laminate pack.

Because the electrical double-layer capacitors of the invention use the quaternary ammonium salt or quaternary phosphonium salt of general formula (1) above as the electrolyte, the ionic conductivity is higher than in prior-art electrical double-layer capacitors, in addition to which the capacitors have a high electrostatic capacitance, excellent low-temperature characteristics and a broad potential window. Moreover, the use of low-impedance polarizable electrodes like those described above makes it possible to endow the capacitor with a high power density and energy density.

Because they are endowed with such characteristics, the electrical double-layer capacitors of the invention are highly suitable for use as a memory backup power supply for cellular phones, notebook computers and wireless terminals, as a power supply for cellular phones and portable acoustic devices, as an uninterruptible power supply for personal computers and other equipment, and as various types of low-current electrical storage devices such as load leveling power supplies used in combination with solar power generation and wind power generation. Moreover, electrical double-layer capacitors capable of being charged and discharged at a high current are highly suitable for use as high-current electrical storage devices in such applications as electric cars and electrical power tools.

Secondary Batteries

The secondary battery of the invention has a positive electrode and a negative electrode, a separator between the positive and negative electrodes, and an electrolyte solution. The electrolyte solution is any of the above-mentioned liquid electrolytes for electrical storage devices to which has been added an ion-conductive salt (liquid electrolytes (2) and (3) described under Liquid Electrolytes for Electrical Storage Devices).

The positive electrode active material making up the positive electrode is suitably selected in accordance with the intended use of the electrode, the type of battery and other considerations. For example, in the case of positive electrodes in lithium secondary cells and lithium ion secondary cells, use can be made of chalcogen compounds capable of occluding and releasing lithium ions, and lithium ion-containing chalcogen compounds.

Examples of such chalcogen compounds capable of occluding and releasing lithium ions include $FeS_2$, $TiS_2$, $MoS_2$, $V_2O_6$, $V_6O_{13}$ and $MnO_2$.

Specific examples of lithium ion-containing chalcogen compounds include $LiCoO_2$, $LiMnO_2$, $LiMn_2O_4$, $LiMo_2O_4$, $LiV_3O_8$, $LiNiO_2$ and $Li_xNi_yM_{1-y}O_2$ (wherein M is one or more metal element selected from among cobalt, manganese, titanium, chromium, vanadium, aluminum, tin, lead and zinc; $0.05 \leq x \leq 1.10$; and $0.5 \leq y \leq 1.0$).

The negative electrode active material making up the negative electrode is suitably selected in accordance with the intended use of the electrode, the type of battery and other considerations. For example, in the case of negative electrodes in lithium secondary cells and lithium ion secondary cells, use can be made of alkali metals, alkali metal alloys, oxides, sulfides or nitrides of at least one element selected from among group 8, 9, 10, 11, 12, 13, 14 and 15 elements of the periodic table capable of reversibly occluding and releasing lithium ions, and carbonaceous materials capable of occluding and releasing lithium ions.

Examples of suitable alkali metals include lithium, sodium and potassium. Examples of suitable alkali metal alloys include metallic lithium, Li—Al, Li—Mg, Li—Al—Ni, sodium, Na—Hg and Na—Zn.

Illustrative examples of the oxides of at least one element selected from periodic table group 8 to 15 elements capable of occluding and releasing lithium ions include tin silicon oxide ($SnSiO_3$), lithium bismuth oxide ($Li_3BiO_4$) and lithium zinc oxide ($Li_2ZnO_2$).

Illustrative examples of the sulfides include lithium iron sulfides $Li_xFeS_2$ (wherein $0 \leq x \leq 3$) and lithium copper sulfides $Li_xCuS$ (wherein $0 \leq x \leq 3$).

Illustrative examples of the nitrides include lithium-containing transition metal nitrides, and specifically $Li_xM_yN$ (wherein M is cobalt, nickel or copper; $0 \leq x \leq 3$; and $0 \leq y \leq 0.5$) and lithium iron nitride ($Li_3FeN_4$).

Examples of carbonaceous materials which are capable of reversibly occluding and releasing lithium ions include graphite, carbon black, coke, glassy carbon, carbon fibers, and sintered bodies obtained from any of these.

The binder polymer and separator which make up the positive and negative electrodes are the same as those described above for electrical double-layer capacitors. Ion-conductive salts that may be used are the conductive salts described above under Liquid Electrolytes for Electrical Storage Devices.

The secondary battery described above can be assembled by stacking, fan-folding or winding a cell assembly composed of a positive electrode and a negative electrode with a separator therebetween. The cell assembly is formed into a coin-like shape, then placed within a battery housing such as a can or a laminate pack. The assembly is then filled with the electrolyte solution, following which the housing is mechanically sealed if it is a can or heat-sealed if it is a laminate pack.

If necessary, a reaction-curable substance such as a (meth) acrylate, an epoxy group-bearing compound or a heat-curable urethane can be added to the electrolyte solution and a reaction carried out to effect curing.

Electrolyte solutions (2) and (3) described above under Liquid Electrolytes can also be used in hybrid-type electrical storage devices in which the positive or negative electrode is a polarizable electrode such as is commonly used in electrical double-layer capacitors and the other, opposing, electrode is an electrode in which the active material is a substance capable of the insertion and extraction of lithium ions, such as is commonly used in lithium ion secondary batteries.

EXAMPLE

Synthesis examples, examples of the invention and comparative examples are given below to more fully illustrate the invention, and are not intended to limit the scope thereof.

Synthesis Example 1

Synthesis of Compound (3)

(3)

A mixed solution prepared by mixing together 100 ml of diethylamine (Kanto Chemical Co., Inc.) and 85 ml of 2-methoxyethyl chloride (Kanto Chemical) was placed in an autoclave and reacted at 100° C. for 24 hours. The internal pressure during the reaction was 1.3 kgf/cm². After 24 hours, 200 ml of an aqueous solution containing 56 g of potassium hydroxide (Katayama Chemical Inc.) was added to the resulting mixture of deposited crystals and reaction solution. The two organic phases that formed as a result were separated off with a separatory funnel and subjected twice to extraction with 100 ml of methylene chloride (Wako Pure Chemical Industries, Ltd.). The separated organic phases were then combined and washed with a saturated saline solution, following which potassium carbonate (Wako Pure Chemical Industries) was added to remove water, and vacuum filtration was carried out. The solvent in the resulting organic phase was distilled off in a rotary evaporator, following which the residue was subjected to normal-pressure distillation, yielding 18.9 g of a fraction that boiled at about 135° C. This compound was confirmed from the ¹H-NMR spectrum to be 2-methoxyethyldiethylamine.

Next, 8.24 g of the 2-methoxyethyldiethylamine was dissolved in 10 ml of tetrahydrofuran (Wako Pure Chemical Industries), following which 4.0 ml of methyl iodide (Wako Pure Chemical Industries) was added under ice cooling. After 30 minutes, the mixture was removed from the ice bath and stirred overnight at room temperature. The solvent in the resulting reaction mixture was then driven off by vacuum distillation, and the resulting solids were recrystallized from an ethanol (Wako Pure Chemical Industries)—tetrahydrofuran system, yielding 16 g of 2-methoxyethyldiethylmethylammonium iodide.

Next, 15.0 g of the 2-methoxyethyldiethylmethylammonium iodide was dissolved in 100 ml of distilled water, following which 6.37 g of silver oxide (Kanto Chemical) was added and stirring was carried out for 3 hours. The reaction mixture was then vacuum filtered to remove the precipitate, following which 42% tetrafluoroboric acid (Kanto Chemical) was gradually added under stirring until the reaction solution reached a pH of about 5 to 6. The reaction solution was subsequently freeze-dried, in addition to which water was thoroughly driven off using a vacuum pump, ultimately yielding 12.39 g of a compound (3) that was liquid at room temperature (25° C.).

FIG. 1 shows the NMR spectrum (solvent: deuterated chloroform) for compound (3).

Synthesis Example 2

Synthesis of Compound (4)

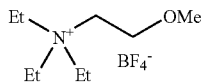

(4)

Aside from using ethyl iodide instead of methyl iodide, compound (4) of the above formula was synthesized in the same way as in Synthesis Example 1. The white crystals obtained after freeze-drying were recrystallized from ethanol to give a pure product.

FIG. 2 shows the NMR spectrum (solvent: deuterated chloroform) for compound (4).

Synthesis Example 3

Synthesis of Compound (5)

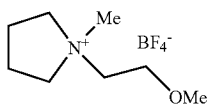

(5)

Aside from using pyrrolidine instead of diethylamine and setting the reaction temperature in the autoclave at 90° C., compound (5) of the above formula was synthesized in the same way as in Synthesis Example 1. The target substance was a liquid at room temperature (25° C.).

FIG. 3 shows the NMR spectrum (solvent: deuterated chloroform) for compound (5).

Synthesis Example 4

Synthesis of Compound (6)

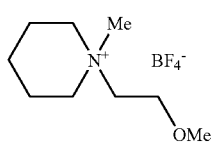

(6)

Aside from using piperazine instead of diethylamine and setting the reaction temperature in the autoclave at 100° C., compound (6) of the above formula was synthesized in the same way as in Synthesis Example 1. The target substance was a liquid at room temperature (25° C.).

FIG. 4 shows the NMR spectrum (solvent: deuterated chloroform) for compound (6).

Synthesis Example 5

Synthesis of Compound (7)

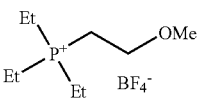

(7)

First, 200 ml of a toluene solution of triethylphosphine (triethylphosphine content, approx. 20%; product of Kanto Chemical) was mixed with 50 ml of 2-methoxyethyl chloride (Kanto Chemical) to effect a reaction, which was carried out under refluxing for 24 hours. The solvent was then distilled off at normal pressure, following which the remaining solvent and unreacted reagents were completed removed by distillation using a vacuum pump. The residue was recrystallized from an ethanol-THF system, yielding 45 g of 2-methoxyethyltriethylphosphonium chloride.

Next, 20.0 g of the 2-methoxyethyltriethylphosphonium chloride thus obtained was dissolved in 100 ml of distilled water, following which 10.89 g of silver oxide (Kanto Chemical) was added and the mixture was stirred for 2 hours. The precipitate was then removed by vacuum filtration, following which 42% tetrafluoroboric acid (Kanto Chemical) was gradually added under stirring until the reaction solution reached a pH of about 5 to 6. The reaction solution was subsequently freeze-dried, in addition to which water was thoroughly driven off using a vacuum pump, yielding 23.87 g of a compound (7) that was liquid at room temperature (25° C.).

Synthesis Example 6

Synthesis of Compound (8)

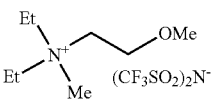

(8)

First, 10.0 g of 2-methoxyethyldiethylmethylammonium iodide obtained by the same method as in Synthesis Example 1 was dissolved in 50 mL of acetonitrile (Kanto Chemical). Next, 9.5 g of lithium bis(trifluoromethanesulfonyl)imide (produced by Kishida Chemical Co., Ltd.) was added and completely dissolved therein, following which the solution was stirred for 15 minutes.

The acetonitrile was removed by vacuum distillation, then water was added to the residue, causing the organic phase to separate into two. The organic phase was then separated off and washed five times with water to remove impurities.

The washed organic phase was subsequently placed under reduced pressure with a vacuum pump and the water was thoroughly driven off, yielding 6.8 g of compound (8) that was liquid at room temperature.

FIG. 5 shows the NMR spectrum (solvent: deuterated chloroform) for compound (8).

Synthesis Example 7

Synthesis of Compound (9)

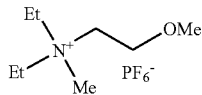
(9)

First, 10.0 g of 2-methoxyethyldiethylmethylammonium iodide obtained by the same method as in Synthesis Example 1 was dissolved in 50 mL of acetonitrile (Kanto Chemical). Next, 9.26 g of silver hexafluorophosphate (supplied by Aldrich Chemical Co., Ltd.) was added and the mixture was stirred for one hour.

The reaction mixture was Celite filtered to remove the solids therein and the solvent was driven off, following which the residue was thoroughly dried under a vacuum, yielding 10.1 g of compound (9) that was liquid at room temperature.

FIG. 6 shows the NMR spectrum (solvent: deuterated chloroform) for compound (9).

Synthesis Example 8

Synthesis of Compound (10)

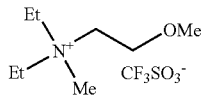
(10)

Aside from substituting silver trifluoromethane sulfonate (Aldrich Chemical) for silver hexafluorophosphate and adding the silver trifluoromethane sulfonate in an amount that is equimolar with the 2-methoxyethyldiethylmethylammoniuom iodide, a compound (10) that is liquid at room temperature (25° C.) was obtained by the same method as in Synthesis Example 7.

FIG. 7 shows the NMR spectrum (solvent: deuterated chloroform) for compound (10).

Synthesis Example 9

Synthesis of Compound (11)

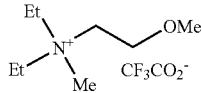
(11)

Aside from using chloroform (Wako Pure Chemical Industries Ltd.) instead of acetonitrile as the solvent, using silver trifluoroacetate (Aldrich Chemical) instead of silver hexafluorophosphate, and adding the silver trifluoroacetate in an amount that is equimolar with the 2-methoxyethyldiethylmethylammoniuom iodide, a compound (11) that was liquid at room temperature (25° C.) was obtained by the same method as in Synthesis Example 7.

FIG. 8 shows the NMR spectrum (solvent: deuterated chloroform) for compound (11).

Examples 1 to 5

Electrical Double-Layer Capacitors

The electrolyte salts prepared in Synthesis Examples 1 to 5 were each dissolved in propylene carbonate (PC) to a concentration of 2.0 M, and the resulting electrolyte solutions were used to manufacture electrical double-layer capacitors in the manner described below.

First, the activated carbon MSP-20 (Kansai Netsukagaku K.K.), an alkali-activated product made from phenolic resin, was mixed with conductive carbon, polyurethane resin and N-methylpyrrolidone (NMP) in a specific ratio (activated carbon/conductive carbon/polyurethane resin/NMP=41.9:3.7:2.2:52.2) to form a paste, thereby giving polarizable electrode compositions for the positive and negative electrodes of electrical double-layer capacitors. The resulting paste-like polarizable electrode compositions were applied onto an aluminum plate with a doctor blade to a dry film thickness of 100 μm, dried at 80° C. for a period of 4 hours, then rolled, thereby giving polarizable electrodes. Each cell was assembled by placing a cellulose-based separator between a pair of the polarizable electrodes. The respective above-described electrolyte solutions were then injected into the assembled cells, giving electrical double-layer capacitors.

Comparative Example 1

Aside from using tetraethylammonium tetrafluoroborate, which is commonly employed as an electrolyte salt for non-aqueous electrical double-layer capacitors, and using a saturated propylene carbonate solution of this electrolyte salt (concentration, about 1.5 M) as the electrolyte solution, electrical double-layer capacitors were manufactured in the same way as in the foregoing examples according to the invention.

Comparative Example 2

Aside from using a solution of tetraethylammonium tetrafluoroborate dissolved in propylene carbonate to a concentration of 1 M as the electrolyte solution, electrical double-layer capacitors were manufactured in the same way as in the above examples of the invention.

Electrostatic Capacitance and Ionic Conductivity:

The electrical double-layer capacitors manufactured in the above examples of the invention and the comparative examples were subjected to a current density charge-discharge test under the conditions shown below, from which the electrostatic capacitance was measured. The ionic conductivity at −20° C. was also measured.

Capacitance Measurement Conditions:

Each electrical double-layer capacitor was charged and discharged at a current density of 1.59 mA/cm$^2$ and a voltage setting of 2.0 to 2.5 V. The capacitor was charged at a constant current; once the voltage reached a predetermined value, charging was continued at that voltage level for at least two hours, following which discharge was carried out at a current density of 1.59 mA/cm$^2$. The capacitance was computed from the integrated value of the electrical energy at discharge. The results are given in Table 1 below.

TABLE 1

| | Electrolyte salt | Electrolyte salt concentration (M) | Capacitance (F/g) | Ionic conductivity at −20° C. (mS/cm) |
|---|---|---|---|---|
| Example 1 | Compound (3) | 2.0 | 32.1 | 7.3 |
| Example 2 | Compound (4) | 2.0 | 31.0 | 6.2 |
| Example 3 | Compound (5) | 2.0 | 33.5 | 6.8 |
| Example 4 | Compound (6) | 2.0 | 31.8 | 5.8 |
| Example 5 | Compound (7) | 2.0 | 30.5 | 5.6 |
| Comparative Example 1 | TEA | Saturated (1.5) | 27.0 | — |
| Comparative Example 2 | TEA | 1.0 | 24.0 | 3.5 |

As is apparent from Table 1, a higher capacitance was achieved in Examples 1 to 5 according to the invention, in which a quaternary ammonium salt or a quaternary phosphonium salt was used as the electrolyte salt, than in the comparative examples.

Moreover, although the salt concentrations in Examples 1 to 5 were higher than in the comparative examples, deposition of the electrolyte salt did not occur. As a result, the ionic conductivities were higher than in Comparative Example 2, demonstrating the usefulness of these capacitors because a greater amount of electrical energy can be drawn at low temperatures. In Comparative Example 1, the electrolyte salt settled out of the electrolyte solution, rendering measurement of the ionic conductivity impossible.

Example 6

Electrical Double-Layer Capacitor

The electrolyte salt prepared in Synthesis Example 1 was dissolved in a mixed solvent of propylene carbonate and ethylene carbonate (PC/EC=9:1) to give an electrolyte solution having a concentration of 2.0 M. Next, two polarizable electrodes (8×16 cm) coated on both sides and two polarizable electrodes (8×16 cm) coated on one side were fabricated. Nickel tab terminals were welded to the electrodes.

Electrical double-layer capacitors were test-built by assembling the polarizable electrodes with the pair of double-sided electrodes stacked together in the middle and a single-sided electrode positioned over each of the two outside surfaces thereof so as to form positive and negative electrodes, and packing these electrodes as a laminate. The resulting electrical double-layer capacitor was subjected to a charge-discharge test. The capacitance, as determined by the energy equivalence method using a discharge curve, was 180 F.

Example 7

Electrical Double-Layer Capacitor (1) Production of Activated Carbon (from polycarbodiimide)

A polycarbodiimide solution was prepared by reacting 54 parts by weight of an 80/20 mixture of 2,4-tolylene diisocyanate and 2,6-tolylene diisocyanate in 500 parts by weight of tetrachloroethylene in the presence of 0.12 part by weight of a carbodiimide catalyst (1-phenyl-3-methyl-phospholene oxide) at 120° C. for a period of 4 hours. The solvent was then driven off by vacuum distillation, yielding a highly viscous liquid polycarbodiimide resin.

The carbodiimide resin was treated at 300° C. for 5 hours and completely solidified, following which it was carbonized by 1 hour of heat treatment at 800° C. The resulting carbide was subjected to steam activation treatment at 900° C. involving the introduction of water at an hourly rate of 5 parts by weight per part by weight of carbide, thereby yielding 6.2 parts by weight of the desired activated carbon.

(2) Manufacture of Electrical Double-Layer Capacitor

Aside from preparing a 2.0 M electrolyte solution by dissolving the electrolyte salt obtained in Synthesis Example 1 in propylene carbonate, and using the activated carbon produced as described above instead of MSP-20 in the polarizable electrodes, an electrical double-layer capacitor was manufactured in the same way as in Example 6.

The resulting electrical double-layer capacitor was subjected to a charge-discharge test. The capacitance, as determined by the energy equivalence method using a discharge curve, was 178 F.

Example 8

Electrical Double-Layer Capacitor

Activated carbon (MSP-20, made by Kansai Netsukagaku K.K.), a conductive material (Denka Black HS100, made by Denki Kagaku Kogyo K.K.) and a binder (PVdF900, made by Kureha Chemical Industry Co., Ltd.) were used as the filler substances in a respective weight ratio of 100:3:5 (based on 100 parts by weight of the activated carbon). These fillers were mixed with N-methyl-2-pyrrolidone (NMP) (grade 1 product, made by Katayama Chemical, Inc.) in a filler-to-NMP weight ratio of 100:212.5 to form a slurry. The slurry was applied onto an aluminum/$AlO_x$ sheet (30CB, made by Japan Capacitor Industrial Co., Ltd.; 250×150×0.030 mm) to a width of 90 mm, then dried (80° C.), rolled (packing density, about 0.7 g/$cm^3$) and cut to dimensions of 50.0 mm (width of coated area, 40.0 mm)×20.0 mm to give electrodes.

Electrodes having a weight of about 0.092 g were selected as positive electrodes and electrodes having a weight of about 0.096 g were selected as negative electrodes. Aluminum tape having a width of 3.0 mm was welded to the positive electrode, and nickel tape having a width of 3.0 mm was welded to the negative electrode.

An electrode group was formed by assembling, in opposition, two positive electrodes and two negative electrodes fabricated as described above, with two cellulose separators (FT40-35, made by Nippon Kodoshi Corporation; thickness, 0.035 mm) cut to dimensions of 54.0×22.0 mm therebetween. A sheet of the above-described 30CB (thickness, 30 μm; 50.0 mm×20.0 mm) with aluminum tape welded thereto was also included in the electrode group as an Al/$AlO_x$ reference electrode, with an intervening separator.

The quaternary salt (ionic liquid) obtained in Synthesis Example 6 was poured as the liquid electrolyte into the above electrode group in a volume equivalent to the volume of the above electrode group (100.0 vol %). The electrolyte-filled electrode group was then placed under a vacuum of about 76 torr for 30 minutes and laminate-packed, giving an electrical double-layer capacitor.

Comparative Example 3

A 1.0 M solution of tetraethylammonium-$BF_4$ in propylene carbonate (LIPASTE-P/EAFIN, produced by Toyama Chemical Co., Ltd.) as the liquid electrolyte was poured into an electrode group obtained in the same way as in Example 8 above to form an electrical double-layer capacitor.

The electrical double-layer capacitors obtained in above Example 8 according to the invention and Comparative Example 3 were subjected to the following electrical tests (1)

to (3) to determine the initial capacitance, the temperature dependence of the discharge properties, and the self-discharge properties.

(1) Initial Capacitance

The following cycle was carried out three times. Charging at 10 mA and 2.5 V to a current cutoff of 1 mA (25° C.), one hour of rest (25° C.), then discharging at 10 mA to a discharge cutoff of 0.0V (25° C.).

(2) Discharge Properties by Temperature

Charging was carried out at 10 mA and 2.5 V to a current cutoff of 1 mA (x° C.), followed by six hours of rest (x° C.), then discharging at 10 mA to a discharge cutoff of 0.0 V (x° C.). The temperature values (x) were −20.0, 0.0, 25.0, 40.0 and 60.0.

(3) Self-Discharge Properties

Charging was carried out at 10 mA and 2.5 V to a current cutoff of 1 mA (25° C.), following which the capacitor was held at 60.0° C.

The results of the above electrical tests are shown in FIGS. 9 to 11.

It is apparent from FIG. 9 that the electrical double-layer capacitor obtained in Example 8 according to the invention achieves substantially the same amount of electricity as the capacitor obtained in the comparative example.

It is thus apparent that even when an ionic liquid is used by itself as the liquid electrolyte, an electrical double-layer capacitor having a performance comparable to that obtained using a conventional organic electrolyte solution can be obtained. Accordingly, from the standpoint of cost and safety, such ionic liquids can be used by themselves as useful liquid electrolytes for electrical storage devices.

Example 9

Secondary Battery (1) Preparation of Electrolyte Solution

An electrolyte solution was prepared by mixing and dissolving 29.2 parts by weight of lithium bis(trifluoromethanesulfonyl)imide in 70.8 parts by weight of the quaternary salt (ionic liquid) obtained in Synthesis Example 6.

(2) Production of Positive Electrode

A paste-like positive electrode composition was prepared by stirring together and mixing the following: 91 parts by weight of $LiCoO_2$ as the positive electrode active material, 3 parts by weight of Ketjenblack as the conductive material, 60 parts by weight of a solution of 10 parts by weight of polyvinylidene fluoride (PVDF) dissolved in 90 parts by weight of N-methyl-2-pyrrolidone, and 15 parts by weight of N-methyl-2-pyrrolidone.

The positive electrode composition was applied onto aluminum foil with a doctor blade to a film thickness when dry of 100 μm. This was followed by 2 hours of drying at 80° C., then rolling to give a $LiCoO_2$ positive electrode.

(3) Production of Lithium Secondary Battery

The positive electrode obtained as described above and metallic lithium as the negative electrode were each cut to a diameter of 12 mm, a polyolefin porous membrane (E25MMS, made by Tonen Tapyrus Co., Ltd.) was placed as the separator between the above 12 mm diameter positive and negative electrodes, and the electrolyte solution prepared as described above was poured and impregnated therein to form a coin-type lithium secondary cell.

Example 10

Secondary Battery

Aside from using an electrolyte solution prepared by mixing and dissolving 90.6 parts by weight of the quaternary salt (ionic liquid) obtained in Synthesis Example 1 and 9.4 parts by weight of lithium tetrafluoroborate, a coin-type lithium secondary battery was manufactured in the same way as in Example 9.

The secondary batteries obtained in above Examples 9 and 10 were subjected to a charge/discharge test in which the upper limit voltage during charging was set at 4.2 V, the voltage cutoff during discharge was set at 3 V, and the current density was 0.025 $mA/cm^2$. The test was carried out by constant-current low-voltage charging and constant-current discharging.

Figure 1:
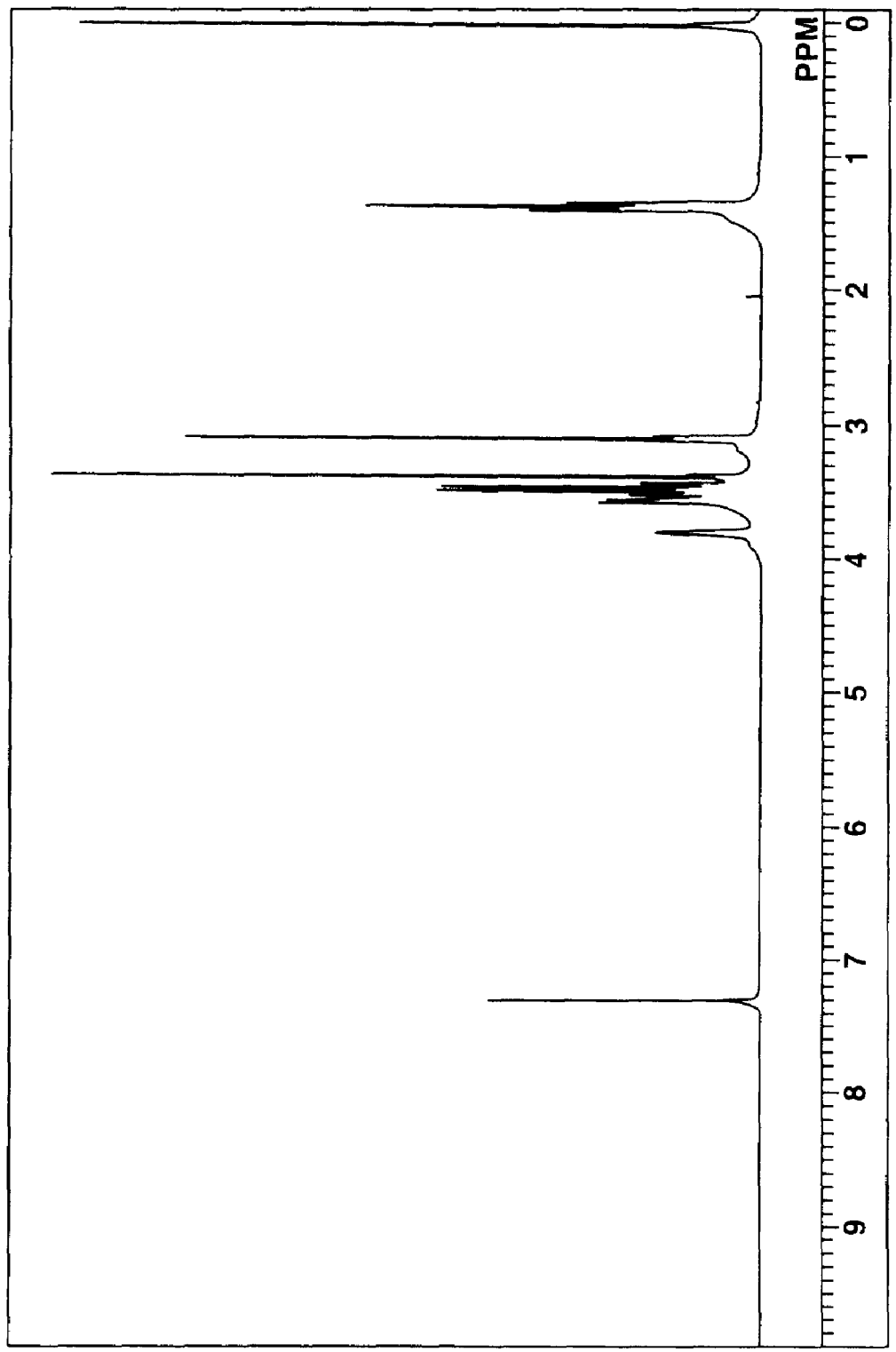
Figure 2:
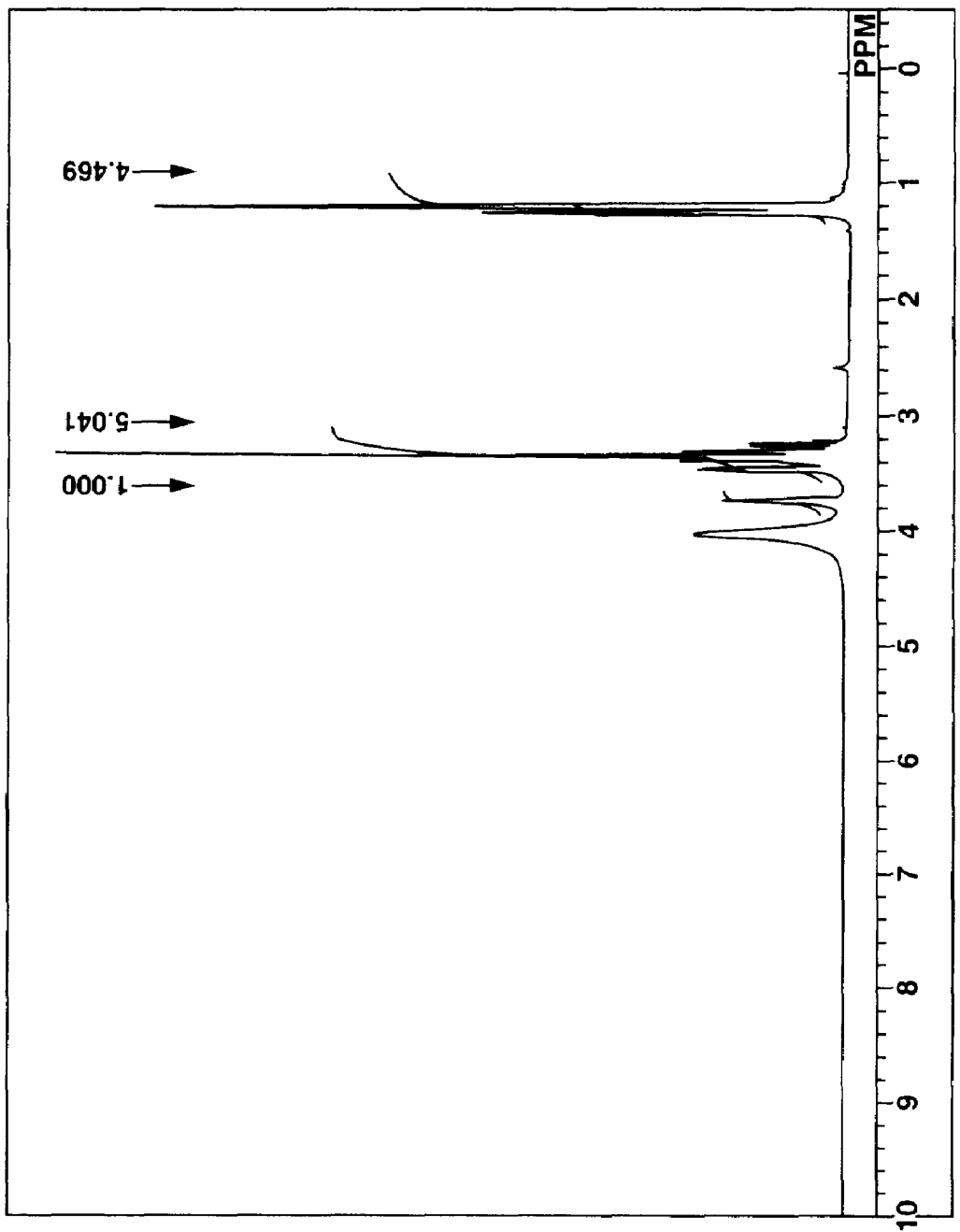
Figure 3:
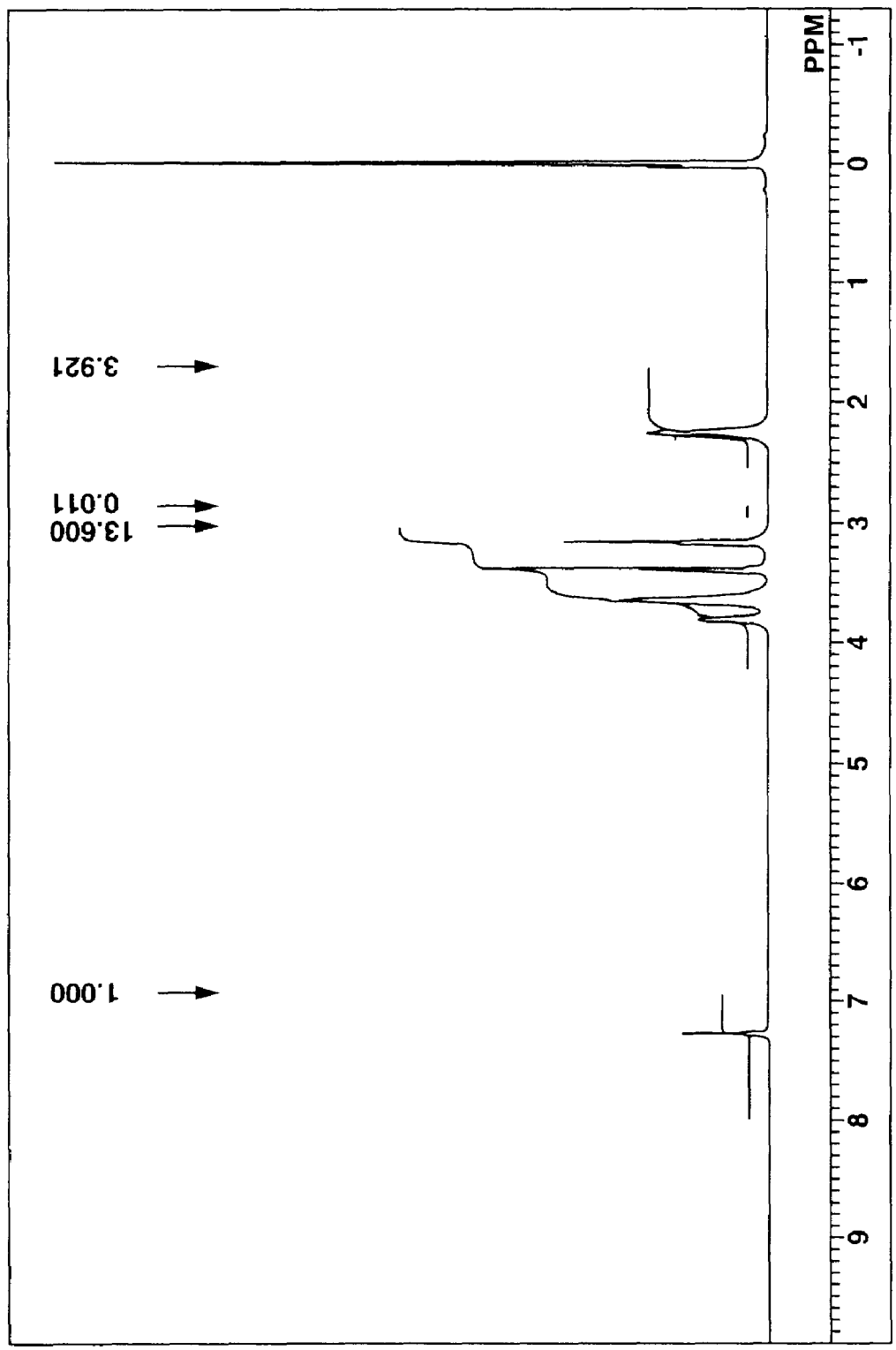
Figure 4:
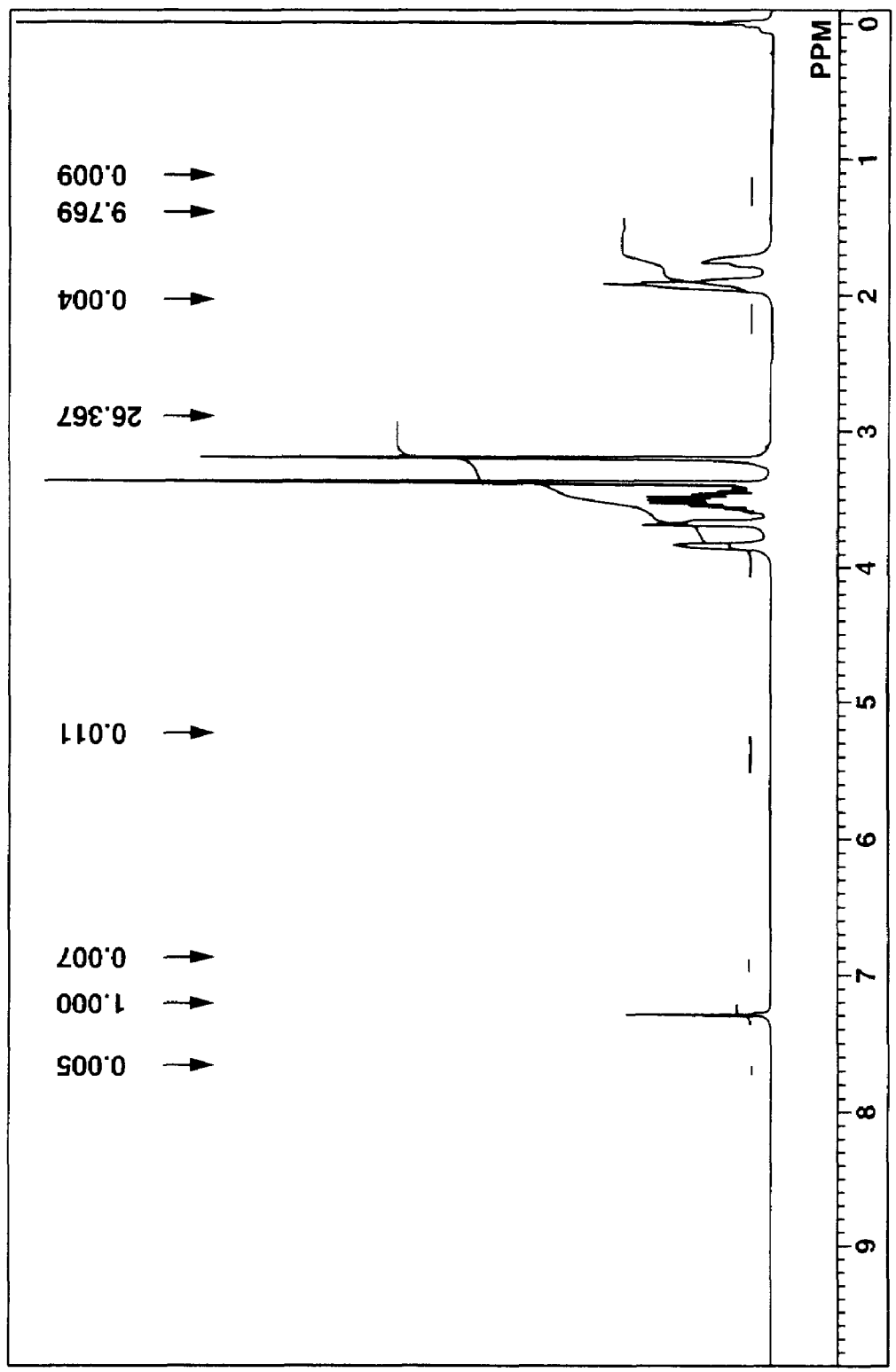
Figure 5:
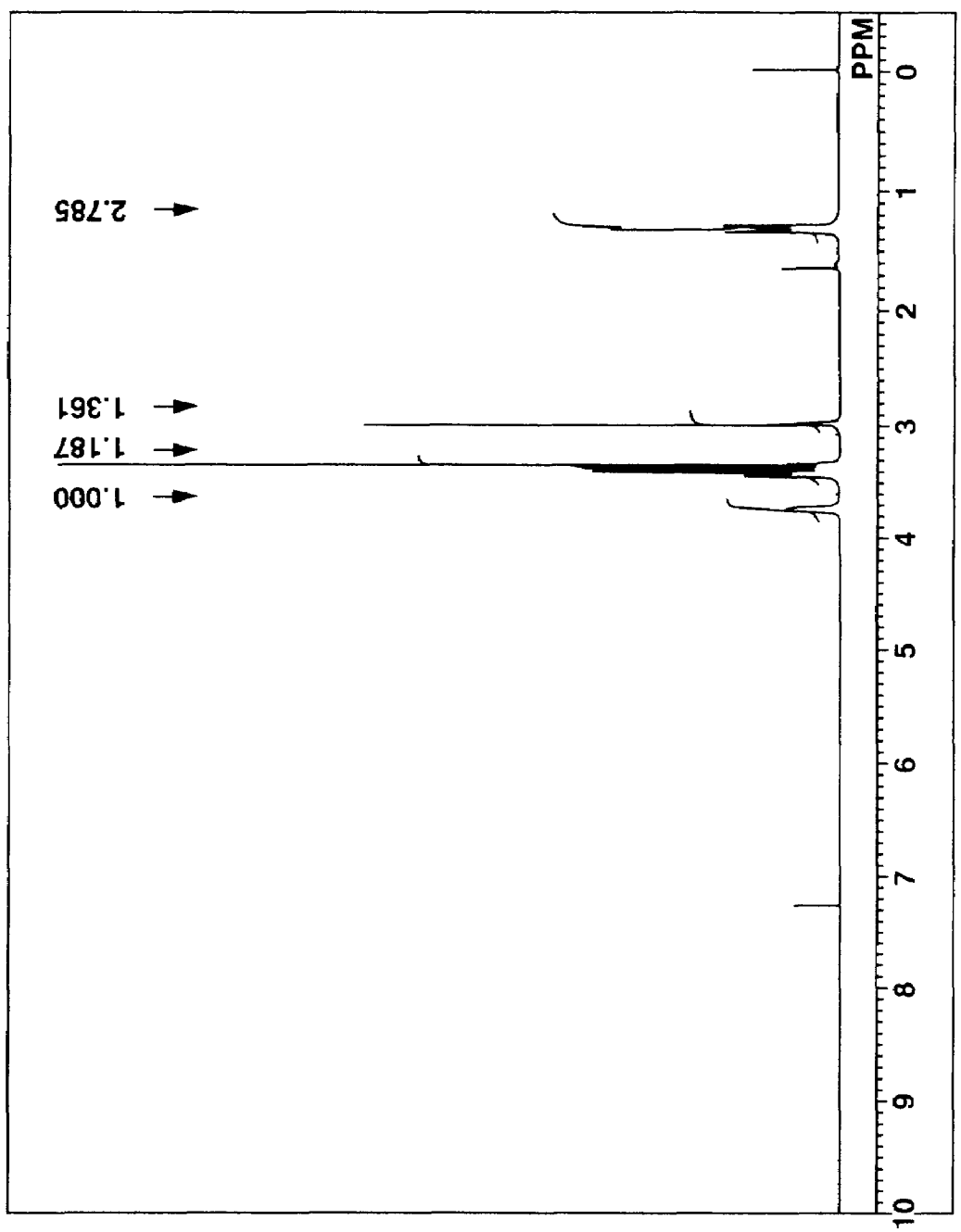
Figure 6:
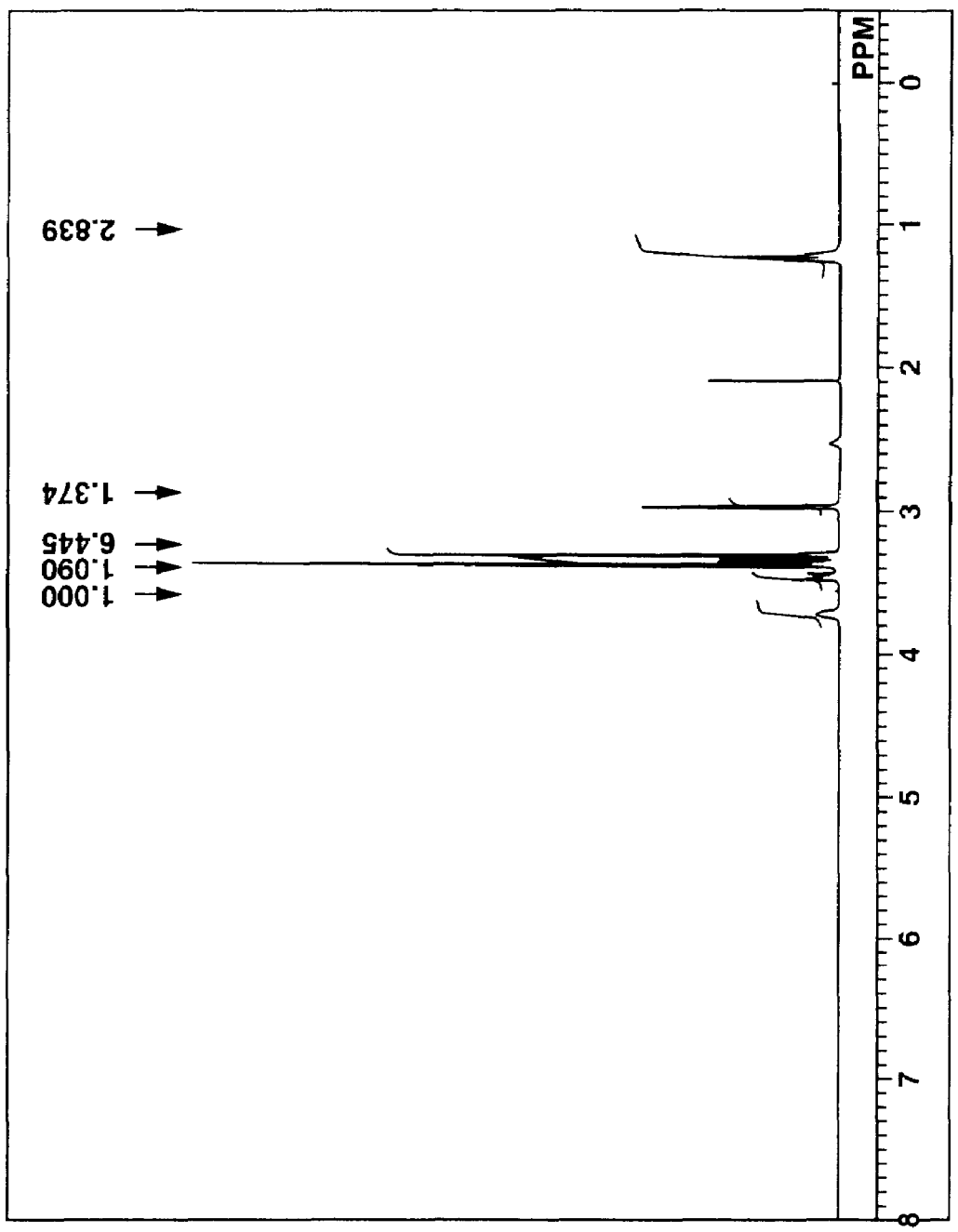
Figure 7:
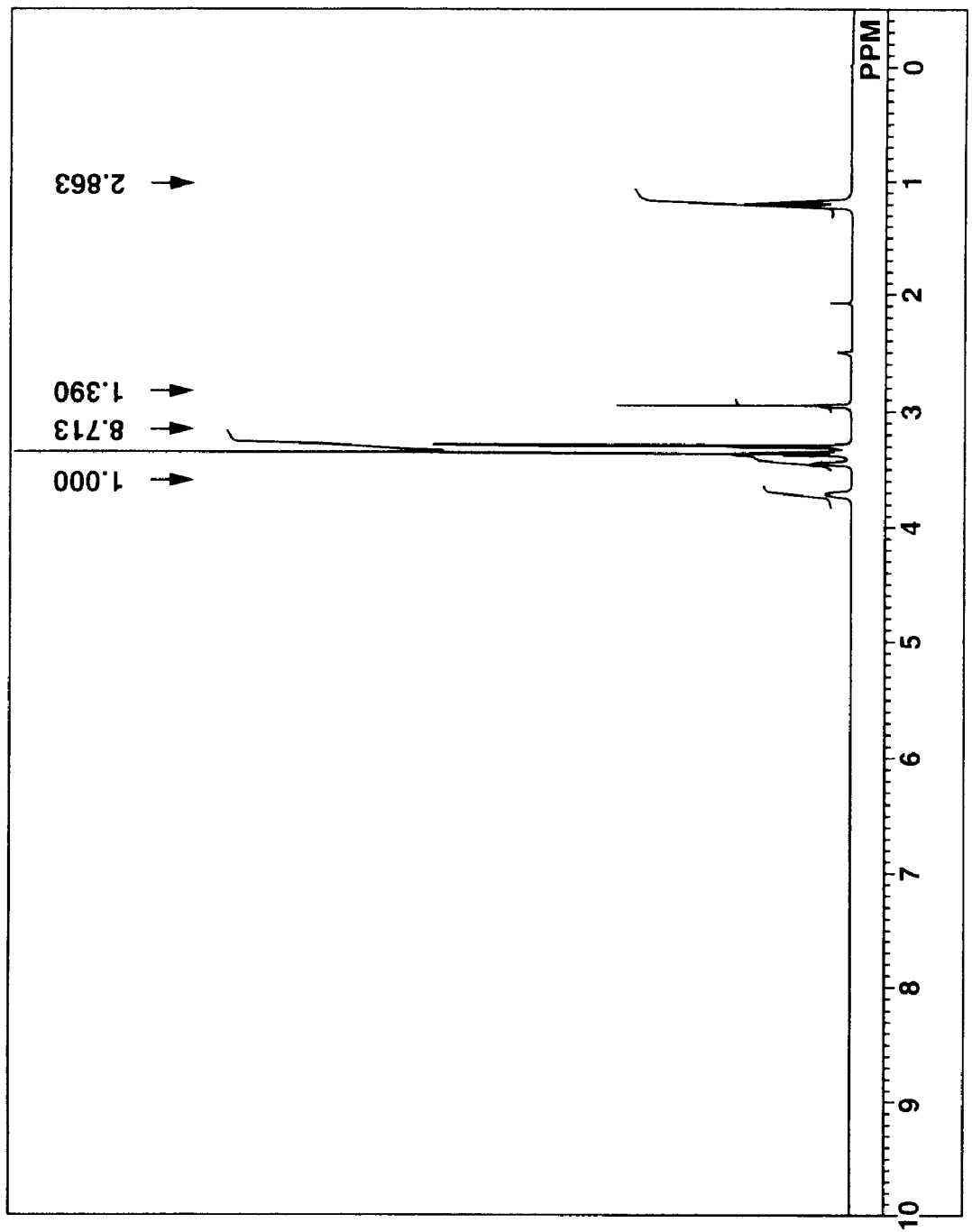
Figure 8:
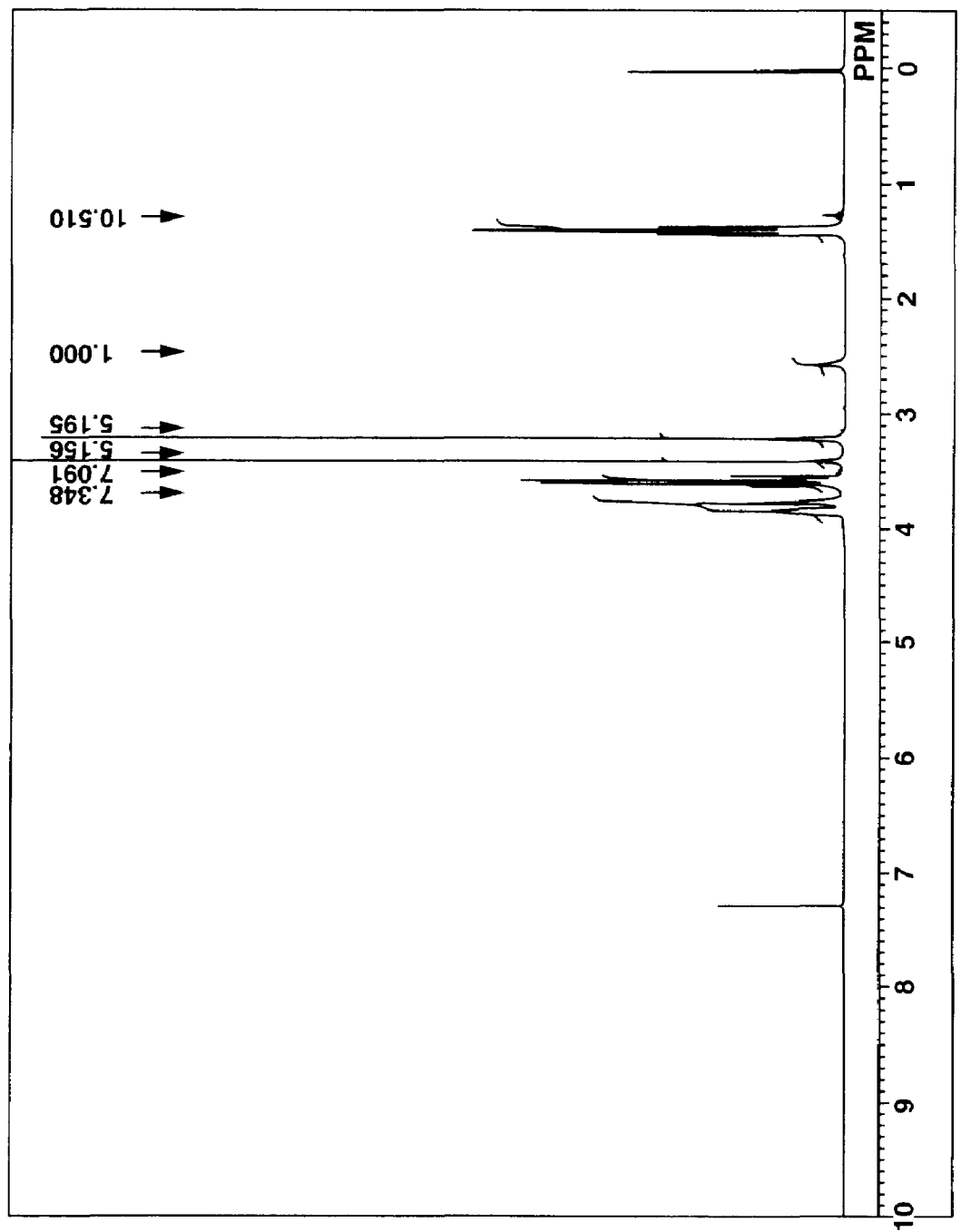
Figure 9:
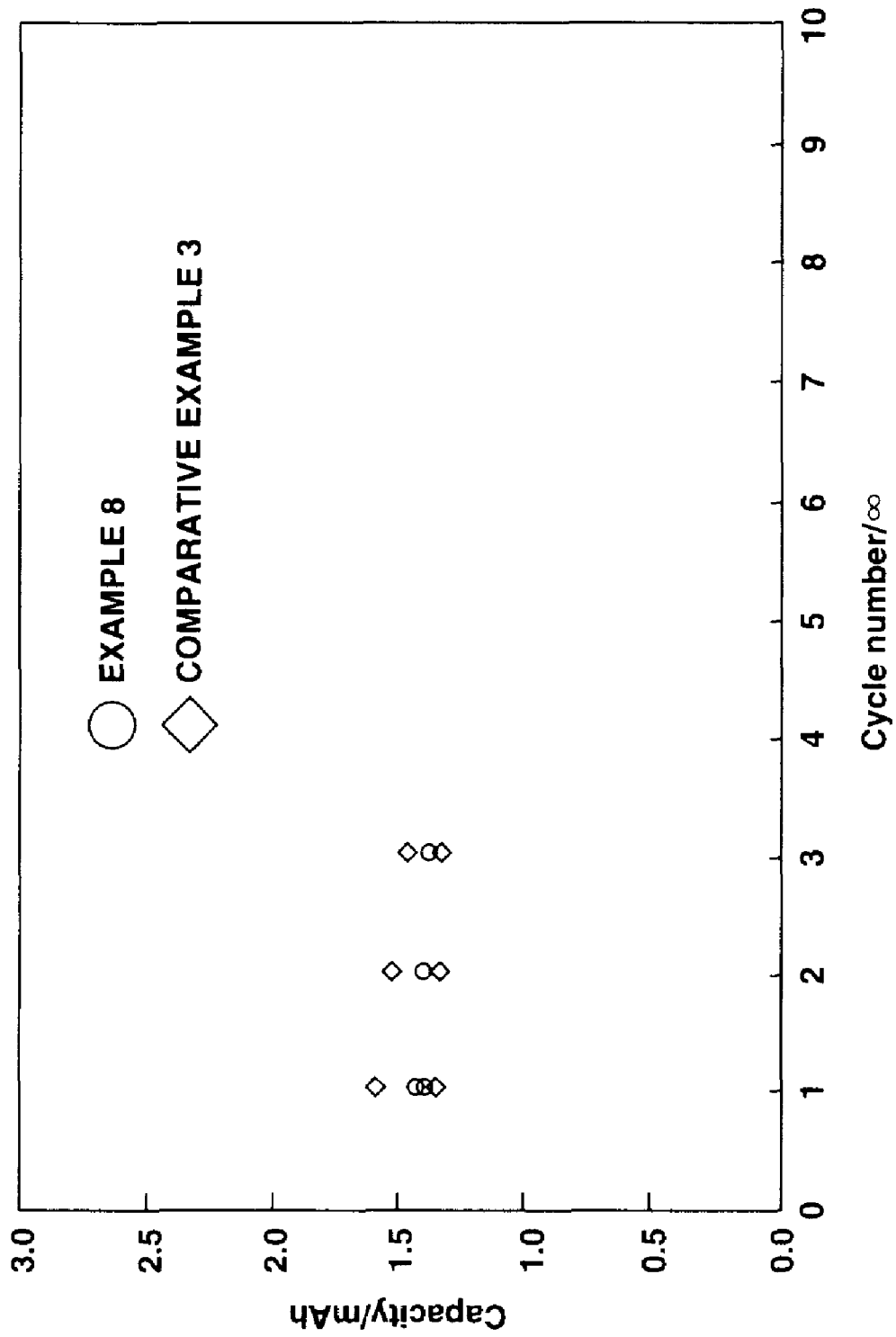
Figure 10:
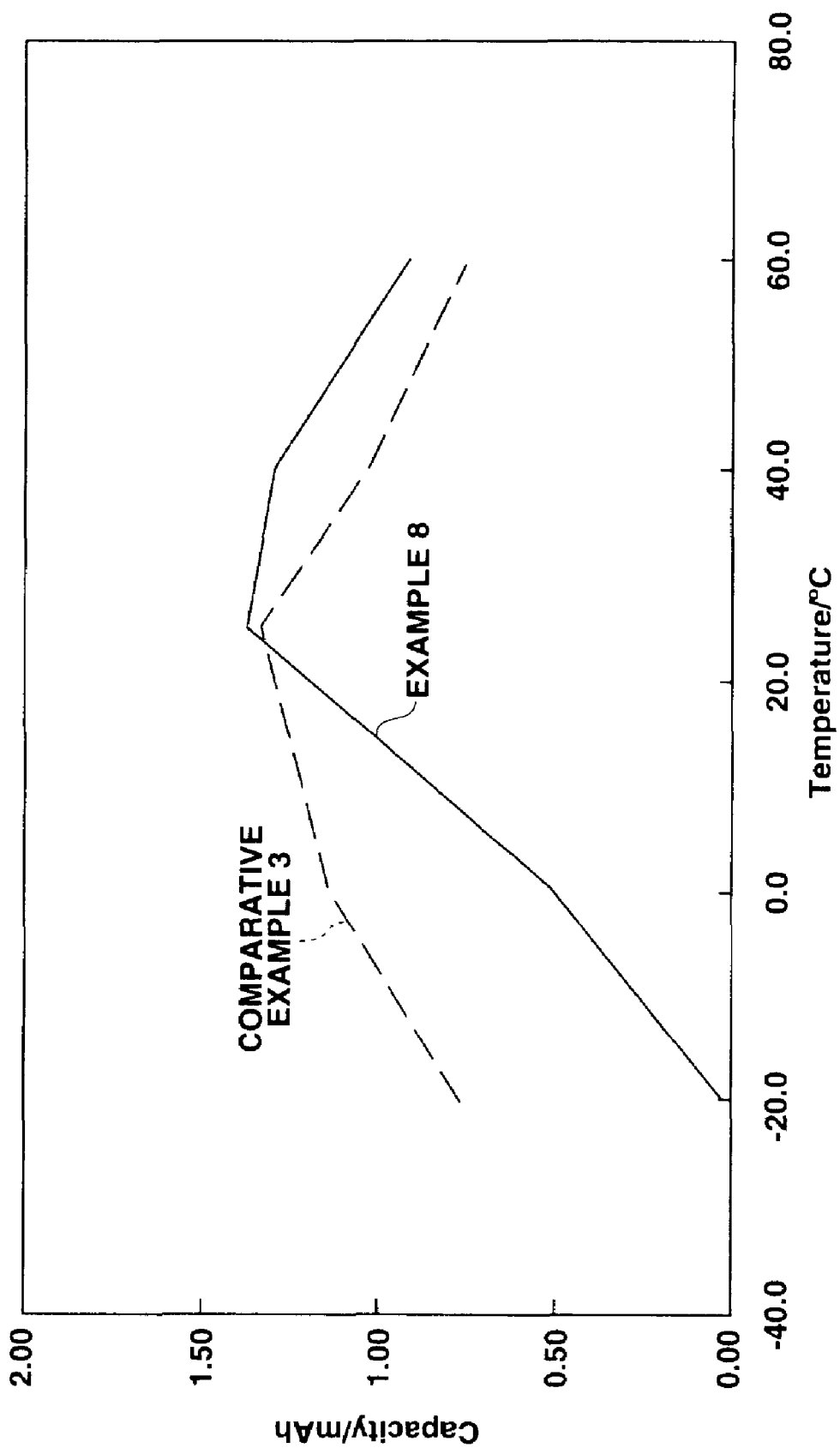
FIG. 10 shows that the electrical double-layer capacitor obtained in Example 8 of the invention does not readily achieve a discharge capacitance on the low-temperature side, but achieves a good discharge capacitance on the high-temperature side.
Figure 11:
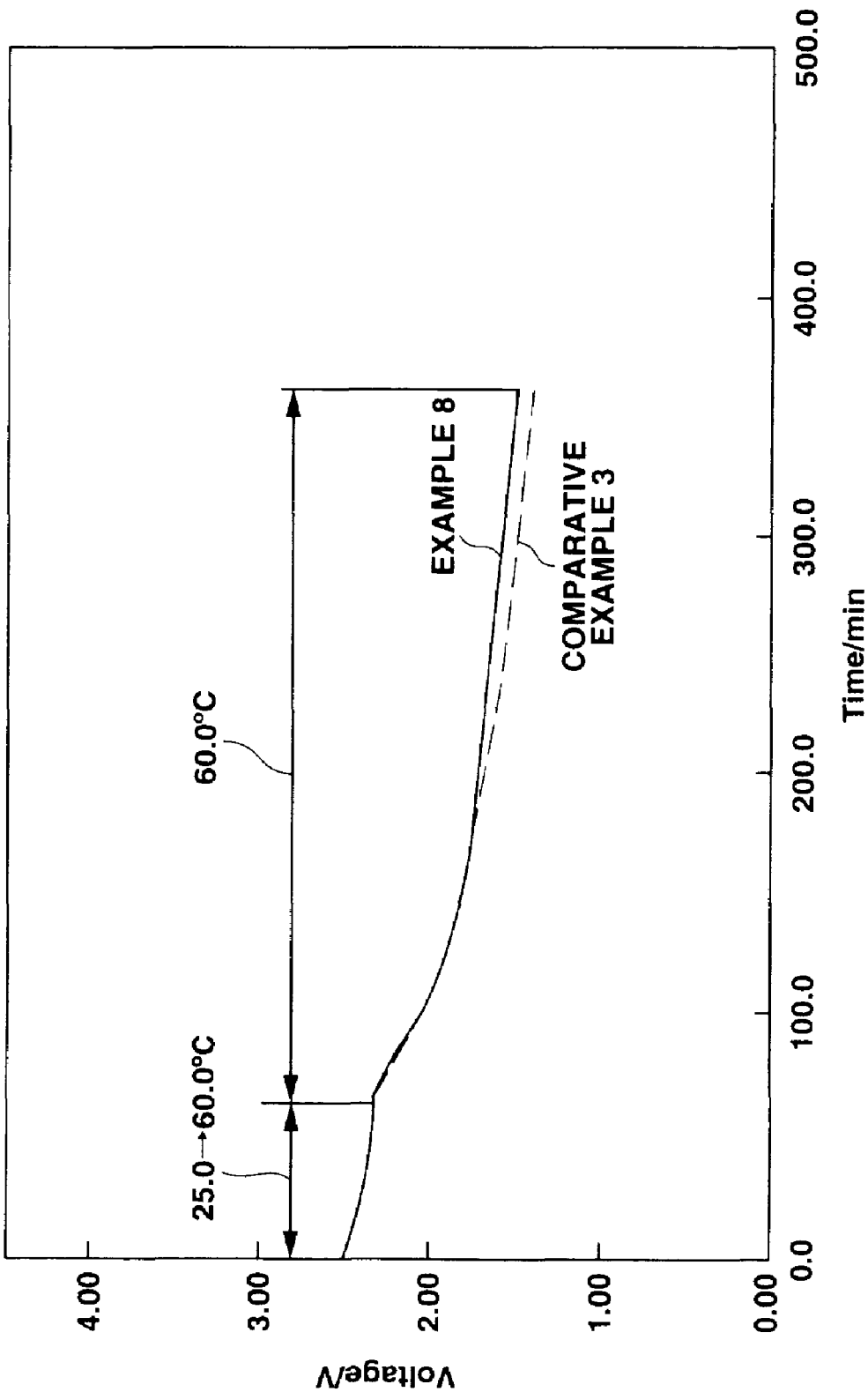
FIG. 11 shows that the electrical double-layer capacitors obtained in Example 8 of the invention and Comparative Example 3 also have comparable self-discharge properties.
Figure 12:
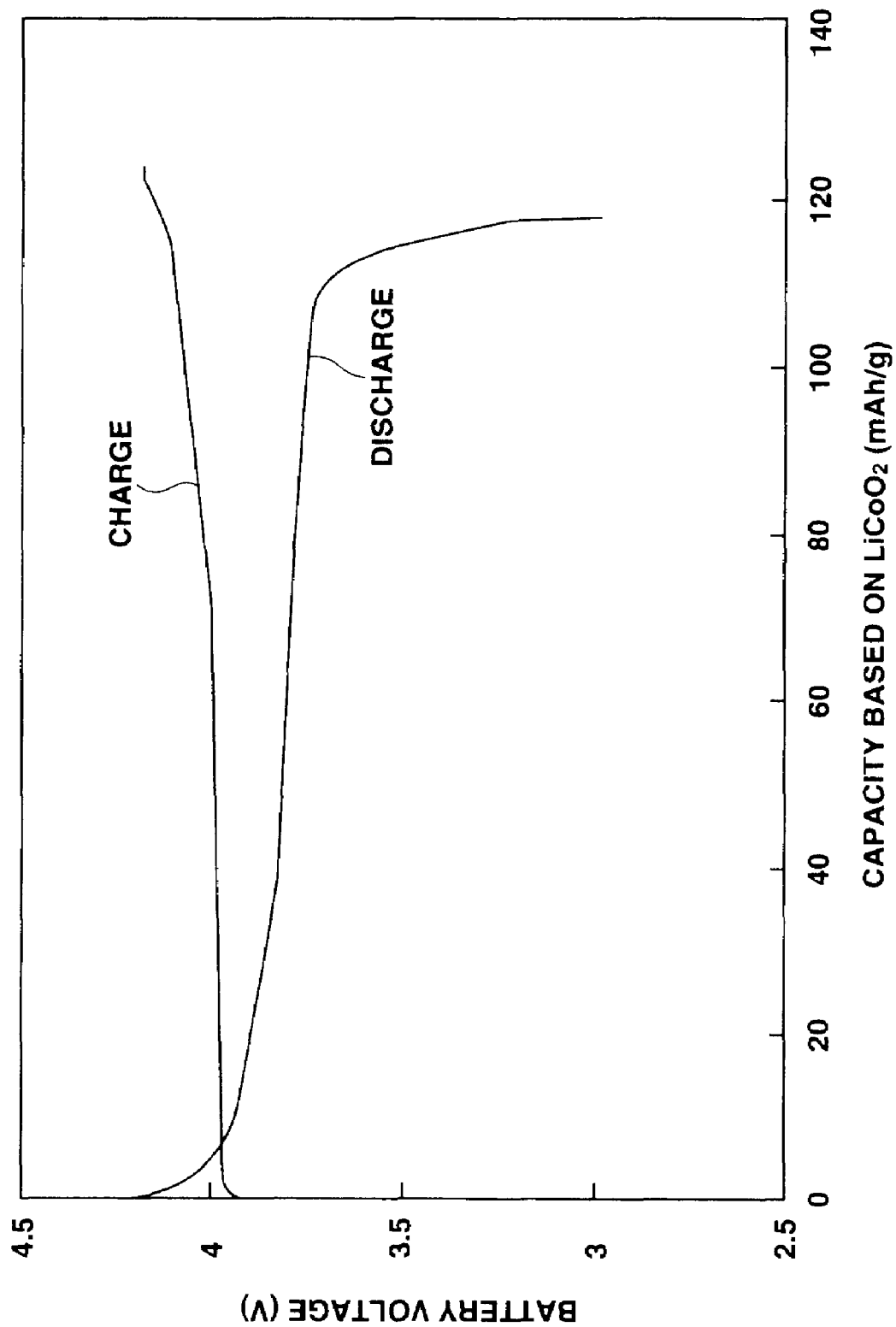

The discharge capacity, based on $LiCoO_2$ in the secondary battery in Example 9, was found to be 117.8 mAh/g, and the discharge capacity based on $LiCoO_2$ in Example 10 was 115.4 mAh/g. Both are adequate values as lithium secondary batteries. FIG. 12 shows a graph of the charge/discharge properties for the secondary battery obtained in Example 9.

As described above, because the electrolyte salt for electrical storage devices according to the invention is a quaternary ammonium salt or quaternary phosphonium salt having at least one alkoxyalkyl group as a substituent thereon, it has a low melting point and excellent solubility in nonaqueous organic solvents. Thus, when liquid electrolytes for electrical storage devices are prepared using these quaternary salts, the liquid electrolyte can be set to a higher concentration than in the prior art and the electrolyte salt does not deposit out at low temperatures. As a result, there can be obtained electrical storage devices (e.g., secondary batteries and electrical double-layer capacitors, as well as other types of capacitors) which have excellent low-temperature properties and have both a high charge/discharge capacitance and a high electrostatic capacitance.

Because the ionic liquids of the invention are easy to manufacture and handle, and have a broader potential window than organic ionic liquids known to the prior art, they lend themselves well to use as novel electrolytes capable of functioning at temperatures below room temperature in the electrodeposition of metals and alloys, in electroplating, and in electrochemical devices for storing energy, such as various types of batteries and capacitors.

The invention claimed is:

1. An electrical double-layer capacitor having:
   a pair of polarizable electrodes,
   a separator between the polarizable electrodes and
   a liquid electrolyte for electrical storage devices comprising an electrolyte salt having general formula (1) below,

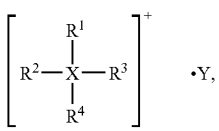

(1)

wherein $R^1$ to $R^4$ are each independently an alkyl of 1 to 5 carbons or an alkoxyalkyl of the formula $R'$—O—$(CH_2)_n$—, $R'$ being methyl or ethyl and the letter n being an integer from 1 to 4, and any two from among $R^1$, $R^2$, $R^3$ and $R^4$ may together form a ring, with the proviso that at least one of groups $R^1$ to $R^4$ is an alkoxyalkyl of the above formula; X is a nitrogen or phosphorus atom; and Y is a monovalent anion.

2. The electrical double-layer capacitor of claim 1, wherein the electrolyte salt is a quaternary salt in which X is a nitrogen atom.

3. The electrical double-layer capacitor of claim 2, wherein the electrolyte salt is a quaternary salt in which X is a nitrogen atom, $R'$ is methyl and the letter n is 2.

4. The electrical double-layer capacitor of claim 1, wherein the electrolyte salt is a quaternary salt having general formula (2) below

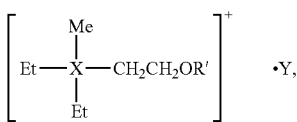

(2)

wherein $R'$ is methyl or ethyl, X is a nitrogen or phosphorus atom, Y is a monovalent anion, Me signifies methyl and Et signifies ethyl.

5. The electrical double-layer capacitor of claim 1, wherein Y is $BF_4^-$, $PF_6^-$, $(CF_3SO_2)_2N^-$, $CF_3SO_3^-$ or $CF_3CO_2^-$.

6. The electrical double-layer capacitor of claim 4, wherein the quaternary salt has general formula (3) below

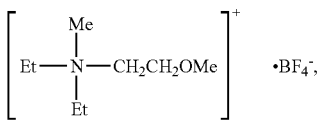

(3)

wherein Me signifies methyl and Et signifies ethyl.

7. The electrical double-layer capacitor of claim 1, wherein the electrolyte salt has a melting point of up to 25° C.

8. The electrical double-layer capacitor of claim 1, wherein the liquid electrolyte is composed solely of the electrolyte salt of general formula (1).

9. The electrical double-layer capacitor of claim 1, wherein the liquid electrolyte for electrical storage devices comprises at least one electrolyte salt of general formula (1) and a nonaqueous organic solvent.

10. The electrical double-layer capacitor of claim 9, wherein the nonaqueous organic solvent is a mixed solvent which includes as a main component ethylene carbonate or propylene carbonate.

11. The electrical double-layer capacitor of claim 9, wherein the nonaqueous organic solvent is one selected from among ethylene carbonate, propylene carbonate, vinylene carbonate, dimethyl carbonate, ethyl methyl carbonate and diethyl carbonate, or a mixed solvent of two or more thereof.

12. The electrical double-layer capacitor of claim 1, wherein the polarizable electrodes include as a main component a carbonaceous material prepared from a resin.

13. The electrical double-layer capacitor of claim 12, wherein the resin is a phenolic resin or a polycarbodiimide resin.

14. The electrical double-layer capacitor of claim 12, wherein the carbonaceous material is prepared by carbonizing a phenolic resin or polycarbodiimide resin, then activating the carbonized resin.

15. The electrical double-layer capacitor of claim 8, further comprising an ion-conductive salt combined with the liquid electrolyte.

16. The electrical double-layer capacitor of claim 15, wherein the ion-conductive salt is a lithium salt.

17. The electrical double-layer capacitor of claim 15, further comprising a nonaqueous organic solvent combined with the liquid electrolyte.

18. A secondary battery having:
a positive electrode and a negative electrode,
a separator between the positive and negative electrodes, and
an electrolyte solution for electrical storage devices,
wherein the electrolyte solution is composed of
an ion-conductive salt which is solid at ambient temperature and
a liquid electrolyte for electrical storage devices which is characterized by being composed solely of an ionic liquid characterized by having general formula (1) below,

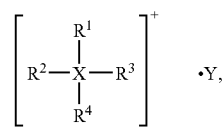

(1)

wherein $R^1$ to $R^4$ are each independently an alkyl of 1 to 5 carbons or an alkoxyalkyl of the formula $R'$—O—$(CH_2)_n$—, $R'$ being methyl or ethyl and the letter n being an integer from 1 to 4, and any two from among $R^1$, $R^2$, $R^3$ and $R^4$ may together form a ring, with the proviso that at least one of groups $R^1$ to $R^4$ is an alkoxyalkyl of the above formula; X is a nitrogen or phosphorus atom; and Y is a monovalent anion.

19. An electrical double-layer capacitor having:
a pair of polarizable electrodes,
a separator between the polarizable electrodes and
an electrolyte solution for electrical storage devices,
wherein the electrolyte solution is composed of
an ion-conductive salt which is solid at ambient temperature and
a liquid electrolyte for electrical storage devices which is characterized by being composed solely of an ionic liquid characterized by having general formula (1) below,

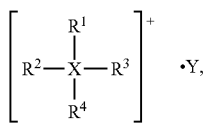

(1)

wherein $R^1$ to $R^4$ are each independently an alkyl of 1 to 5 carbons or an alkoxyalkyl of the formula R'—O—$(CH_2)_n$—, R' being methyl or ethyl and the letter n being an integer from 1 to 4, and any two from among $R^1$, $R^2$, $R^3$ and $R^4$ may together form a ring, with the proviso that at least one of groups $R^1$ to $R^4$ is an alkoxyalkyl of the above formula; X is a nitrogen or phosphorus atom; and Y is a monovalent anion.

20. An electrical storage device having:

a positive electrode composed of activated carbon, a negative electrode composed of a carbonaceous material that is capable of occluding and releasing lithium ions, and an electrolyte solution for electrical storage devices, wherein the electrolyte solution is composed of an ion-conductive salt which is solid at ambient temperature and a liquid electrolyte for electrical storage devices which is characterized by being composed solely of an ionic liquid characterized by having general formula (1) below,

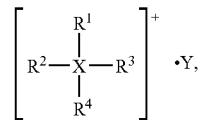

(1)

wherein $R^1$ to $R^4$ are each independently an alkyl of 1 to 5 carbons or an alkoxyalkyl of the formula R'—O—$(CH_2)_n$—, R' being methyl or ethyl and the letter n being an integer from 1 to 4, and any two from among $R^1$, $R^2$, $R^3$ and $R^4$ may together form a ring, with the proviso that at least one of groups $R^1$ to $R^4$ is an alkoxyalkyl of the above formula; X is a nitrogen or phosphorus atom; and Y is a monovalent anion.

* * * * *